US010258619B2

(12) United States Patent
Molineaux et al.

(10) Patent No.: US 10,258,619 B2
(45) Date of Patent: Apr. 16, 2019

(54) COMBINATION THERAPY WITH GLUTAMINASE INHIBITORS AND IMMUNO-ONCOLOGY AGENTS

(71) Applicant: Calithera Biosciences, Inc., South San Francisco, CA (US)

(72) Inventors: Susan M. Molineaux, San Francisco, CA (US); Matthew I. Gross, San Francisco, CA (US); Susan D. Bromley, San Francisco, CA (US); Francesco Parlati, San Francisco, CA (US); Mark K. Bennett, Moraga, CA (US)

(73) Assignee: Calithera Biosciences, Inc., South San Francisco, CA (US)

( * ) Notice: Subject to any disclaimer, the term of this patent is extended or adjusted under 35 U.S.C. 154(b) by 0 days.

(21) Appl. No.: 15/284,865

(22) Filed: Oct. 4, 2016

(65) Prior Publication Data

US 2017/0095473 A1 Apr. 6, 2017

Related U.S. Application Data

(60) Provisional application No. 62/323,179, filed on Apr. 15, 2016, provisional application No. 62/237,287, filed on Oct. 5, 2015.

(51) Int. Cl.
| | | |
|---|---|---|
| *A61K 31/501* | (2006.01) | |
| *A61K 38/17* | (2006.01) | |
| *A61K 39/395* | (2006.01) | |
| *A61K 45/06* | (2006.01) | |
| *C07K 16/28* | (2006.01) | |
| *A61K 39/00* | (2006.01) | |

(52) U.S. Cl.
CPC ........ *A61K 31/501* (2013.01); *A61K 38/1774* (2013.01); *A61K 39/3955* (2013.01); *A61K 45/06* (2013.01); *C07K 16/2818* (2013.01); *C07K 16/2827* (2013.01); *A61K 2039/505* (2013.01); *C07K 2317/73* (2013.01); *C07K 2317/76* (2013.01)

(58) Field of Classification Search
CPC .................................................. A61K 31/501
See application file for complete search history.

(56) References Cited

U.S. PATENT DOCUMENTS

| | | |
|---|---|---|
| 6,451,828 B1 | 9/2002 | Newcomb et al. |
| 8,604,016 B2 | 12/2013 | Li et al. |
| 8,865,718 B2 | 10/2014 | Li et al. |
| 9,687,485 B2 | 6/2017 | Steggerda et al. |
| 9,938,267 B2 | 4/2018 | Li et al. |
| 2002/0115698 A1 | 8/2002 | Newcomb et al. |
| 2005/0260697 A1 | 11/2005 | Wang et al. |
| 2010/0330197 A1 | 12/2010 | Higashiguchi et al. |
| 2012/0302605 A1 | 11/2012 | DeWitt |
| 2013/0109643 A1 | 5/2013 | Riggins et al. |
| 2014/0050699 A1 | 2/2014 | Li et al. |
| 2014/0142081 A1 | 5/2014 | Lemieux et al. |
| 2014/0142146 A1 | 5/2014 | Lemieux et al. |
| 2014/0194421 A1 | 7/2014 | Li et al. |
| 2014/0369961 A1 | 12/2014 | Li et al. |
| 2015/0004134 A1 | 1/2015 | Bennett et al. |
| 2015/0258082 A1 | 9/2015 | Parlati et al. |
| 2016/0010158 A1 | 1/2016 | Wang et al. |
| 2016/0022674 A1 | 1/2016 | Steggerda et al. |
| 2016/0287564 A1 | 10/2016 | Gross et al. |
| 2017/0333430 A1 | 11/2017 | Steggerda et al. |
| 2018/0055825 A1 | 3/2018 | Liang et al. |
| 2018/0055842 A1 | 3/2018 | Bennett et al. |
| 2018/0055843 A1 | 3/2018 | Parlati et al. |

FOREIGN PATENT DOCUMENTS

| | | |
|---|---|---|
| WO | WO-2011143160 A2 | 11/2011 |
| WO | WO-2012006506 A1 | 1/2012 |
| WO | WO-2013/044596 A1 | 4/2013 |
| WO | WO-2013078123 A1 | 5/2013 |
| WO | WO-2014039960 A1 | 3/2014 |
| WO | WO-2014/078645 A1 | 5/2014 |
| WO | WO-2014/079136 A1 | 5/2014 |
| WO | WO-2014/081925 A1 | 5/2014 |
| WO | WO-2014089048 A1 | 6/2014 |
| WO | WO-2015061432 A1 | 4/2015 |
| WO | WO-2015061752 A1 | 4/2015 |
| WO | WO-2015/138902 A1 | 9/2015 |
| WO | WO-2015/192014 A1 | 12/2015 |
| WO | WO-2016/004418 A1 | 1/2016 |
| WO | WO-2016/014890 A1 | 1/2016 |
| WO | WO-2016/022969 A1 | 2/2016 |
| WO | WO-2016/054388 A1 | 4/2016 |
| WO | WO-2016/077632 A2 | 5/2016 |

(Continued)

OTHER PUBLICATIONS

Cancer and Metastasis Reviews (1998), 17(1), 91-106.* Science (1999), vol. 286, 531-537.*
Cancer [online], [retrieved on Jul. 6, 2007]. Retrieved from the internet, URL http://www.nlm.nih.gov/medlineplus/cancer.html>.*
Das et al., "Anti-myeloma activity of a novel glutaminase inhibitor CB-839," Blood, vol. 124(21): 4226 (2014).
Liu et al., "Screening for EGFR and KRAS Mutations in Non-Small Cell Lung Carcinomas using DNA Extraction by Hydrothermal Pressure Coupled with PCR-based Direct Sequencing," Int J Clin Exp Pathol, 6(9): 1880-1889 (2013).
International Search Report and Written Opinion for Application No. PCT/US2016/055316 dated Jan. 12, 2017.

(Continued)

*Primary Examiner* — Shawquia Jackson
(74) *Attorney, Agent, or Firm* — David P. Halstead; Foley Hoag LLP

(57) ABSTRACT

The invention relates to methods of treating cancer, myeloproliferative diseases, or immunological or neurological diseases with a combination of a glutaminase inhibitor and an immuno-oncology therapeutic agent, such as an inhibitor of arginase, CTLA-4, indoleamine 2,3-dioxygenase, and/or PD-1/PD-L1.

20 Claims, 4 Drawing Sheets

(56) References Cited

FOREIGN PATENT DOCUMENTS

| | | |
|---|---|---|
| WO | WO-2016/160980 A1 | 10/2016 |
| WO | WO-2016/164401 A1 | 10/2016 |

OTHER PUBLICATIONS

Borodovsky et al., "5-azacytidine reduces methylation, promotes differentiation and induces tumor regression in a patient-derived IDH1 mutant glioma xenograft," Oncotarget, 4(10): 1737-1737 (Sep. 16, 2013).
Bromley-Dulfano, et al., "Antitumor activity of the glutaminase inhibitor CB-839 in hematological malignances," Blood, 122(21): 4226 (2013).
CAS RN 1400068-83-8 STN Entry Date Oct. 8, 2012; N,N1-(5,51-(pentane-1,5-diyl)]bis(1,3,4-thiadiazole-5,2-diyl))bis(2-methoxybenzamide).
CAS RN 331234-76-5, STN Entry Date Apr. 13, 2001; N,N1-[thiobis(2,1-ethanediyl-1,3,4-thiadiazole-5,2-diyl)]bis-1H-1,2,4-triazole-3-carboxmide.
Chemical Abstract Registry No. 296888-91-0, indexed in the Registry File on STN CAS Online Oct. 18, 2000.
Chemical Abstract Registry No. 666208-63-5, indexed in the Registry File on STN CAS Online Mar. 22, 2004.
Costello et al., "Evidence for changes in RREB-1, ZIP3, and zinc in the early development of pancreatic adenocarcinoma," J Gastrointest Cancer, 43:570-6 (2012).
Dai et al., "Studies on the novel a-glucosidase inhibitory activity and structure-activity relationships for andrographolide analogues," Bioorg Med Chem Lett, 16:2710-13 (2006).
DeLabarre B. a et al., "Full-Length Human Glutaminase in Complex with an Allosteric Inhibitor", Biochem, 50:1-27 (2011).
Gehlen H. et al., "Uber die Einwirkung von Isocyanaten auf substituierte 2-Amino-1,3,4-oxdiazole", Justus Leibigs Annalen der Chemie, vol. 692, pp. 151-165 (1966).
Gehlen, H., et al. "Uber die Acylierung der 2-Amino-5-(alkyl, aryl)-1.3.4-oxidazole," Leibeigs Ann. Chem. 703: 131-135 (1967).
Gennaro, A., Remington's Pharmaceutical Sciences. Easton, PA:Mack Pub. Co., 1990.
Gross et al., "Antitumor Activity of the Glutaminase Inhibitor CB-839 in Triple-Negative Breast Cancer", Mol. Cancer Ther., 13(4):890-901 (2014).
Hensley et al., "Glutamine and cancer: Cell biology, physiology, and clinical opportunities," J Clin Investig, 123(9):3678-84 (2013).
Holliday et al., "Choosing the right cell line for breast cancer research," Breast Cancer Res, 13:215 (2011).
Horig et al., "From bench to clinic and back: Perspective on the 1st IQPC Translational Research conference", Journal of Translational Medicine, vol. 2, p. 44 (2004).
International Search Report for Application No. PCT/US2016/026127, dated Jul. 27, 2016.
Ito et al., "A medium-term rat liver bioassay for rapid in vivo detection of carcinogenic potential of chemicals," Cancer Science, 94(1):3-6 (2003).
Jacque, et al., "Targeting glutaminolysis has antileukemic activity in acute myeloid leukemia and synergizes with BCL-2 inhibition," Blood, 126(11): 1346-1356 (2015).
Johnson et al., "Relationships between drug activity and NCI preclinical in vitro and in vivo models and early clinical trials," Brit J Cancer, 84(10):1424-31 (2001).
Kim, A., "Clinical impact of gene expression profiling on oncology diagnosis, prognosis, and treatment," Combinatorial Chem & High Throughput Screening, 7:183-206 (2004).
Kung et al., "Glutamine synthetase is a genetic determinant of cell type-specific glutamine independence in breast epithelia," PLOS Genetics, 7(8):e1002229 (2011).
Martin et al., "Do structurally similar molecules have similar biological activity?" J Med Chem, 45:4350-8 (2002).
Mc,Cleland, et al., "Lactate dehydrogenase B is required for the growth of KRAS-Dependent lung adenocarcinomas," Clin Cancer Res, 19(4): 773-784 (2013).
Medina, M., "Glutamine and cancer," J Nutr, 131(9 Suppl):2539S-42S (2001).
Osol, A. [Editor]. "Chapter 27: Structure-activity relationship and drug design," Remington's Pharmaceutical Sciences (Sixteenth Edition). 1980. pp. 420-435.
Pajic et al., "Cell cycle activation by c-myc in a Burkitt's lymphoma model cell ine", International Journal of Cancer, vol. 87, pp. 787-793 (2000).
Parlati et al., "Antitumor Activity of the Glutaminase Inhibitor CB-839 in Hematological Malignances", 55th ASH Annual Meeting and Exposition, Dec. 9, 2013, New Orleans, LA, abstract No. 4226.
Prat et al., "Phenotypic and molecular characterization of the claudin-low intrinsic subtype of breast cancer," Breast Cancer Res, 12(5):R68 (2010).
Rajagopalan K.N. et al., "Role of Glutamine in Cancer: Therapeutic and Imaging Implications", Journal of Nuclear Medicine, vol. 52, pp. 1005-1008 (2011).
Robinson et al., "Novel mechanism of inhibition of rat kidney-type glutaminase by bis-2-(5-phenylacetamido-1,2,4-thiadiazol-2-yl)ethyl sulfide (BPTES)," Biochem. J., 406:407-414 (2007).
Schäfer et al., "Failure is an option: learning from unsuccessful proof-of-concept trials", Drug Discovery Today, vol. 13, pp. 913-916 (2008).
Seltzer et al., "Inhibition of glutaminase preferentially slows growth of glioma cells with mutant IDH1", Cancer Research, vol. 70, pp. 8981-8987 (2010).
Shimano Y. et al., "Synthesis of Poly(diacylthiosemicarbazide)s from Diacylisothiocyanates and Dihydrazides, and Their Thermal Cyclodehydration" Kobunshi Ronbunshu, vol. 37, No. 2, pp. 131-137 (1980).
Shukla, K., et al, "Design, Synthesis and Pharmacological Evaluation of Bis-2-(5-phenylacetamido-1-2, 4-thiadiazol-2-yl)ethyl 1 sulphide 3 (BPTES) Analogs as Glutaminase Inhibitors", Journal of Medicinal Chemistry, vol. 55, No. 23, pp. 10551-10563 (2012).
Simpson et al., "Modifying metabollically sensitive histone marks by inhibiting glutamine metabolism affects gene expression and alters cancer cell phenotype," Epigenetics, 7(12):1413-20 (2012).
Sporn et al., "Chemoprevention of cancer," Carcinogenesis, 21(3):525-30 (2000).
Thangavelu, K. et al., "Structural basis for the allosteric inhibitory mechanism of human kidney-type glutaminase (KGA) and its regulation by Raf-Mek-Erk signaling in cancer cell metabolism", Proceedings of the National Acedemy of Sciences of the United States of America, vol. 109, No. 20, pp. 7705-7710 (2012).
Thoppil et al., "Terpenoids as potential chemopreventive and therapeutic agents in liver cancer," World J Hepatol, 3(9):228-249 (2011).
Tseng, et al., "The synthesis of daidzein derivatives," J Natural Taiwan Normal University, 30: 537-545 (1985).
Voskoglou-Nomikos et al., "Clinical predictive value of the in vitro cell line, human xenograft, and mouse allograft preclinical cancer models," Clin Cancer Res, 9:4227-39 (2003).
Wang et al., "Targeting mitochondrial glutaminase activity inhibits oncogenic transformation," Cancer Cell, 18(3):207-19 (2010).
Written Opinion of the International Searching Authority for Application No. PCT/US2016/026127, dated Jul. 27, 2016.
Zimmerman, et al., "Allosteric glutaminase inhibitors based on a 1,4-Di(5-amino-1,3,4-thiadiazol-2-yl)butane scaffold," ACS Med Chem Lett, 7(5): 520-524 (2016).
Parlati et al., "Glutaminase inhibitor CB-839 synergizes with pomalidomide in preclinical multiple myeloma models," American Society of Hematology Annual Meeting—Dec. 6-9, 2014.
Nars et al., "Immunomodulatory effects of low dose chemotherapy and perspectives of its combination with immunotherapy," Int J Cancer, 132(11):2471-2478 (2013).
Lopez-Girona et al., "Cereblon is a direct protein target for immunomodulatory and antiproliferative activities of lenalidomide and pomalidomide," Leukemia, 26(11):2326-2335 (2012).

(56) References Cited

OTHER PUBLICATIONS

Lacy et al., "Pomalidomide (CC4047) plus low dose dexamethasone (Pom/dex) is active and well tolerated in lenalidomide refractory multiple myeloma (MM)," Leukemia, 24(11): 1934-1939 (2010).
CAS Registry No. 714283-67-7 STN Entry Date Jul. 22, 2004.
Haynes et al., "Occurrence of Pharmaceutically Acceptable Anions and Cations in the Cambridge Structural Database," J Pharm Sci, 94: 2111-2120 (2005).
Toppmeyer et al., "Safety and efficacy of the multidrug resistance inhibitor Incel (biricodar; VX-710) in combination with paclitaxel for advanced breast cancer refractory to paclitaxel," Clin Cancer Res, 8(3):670-678 (2002).
Study of the Glutaminase Inhibitor CB-839 in Solid Tumors. National Institute of Health. U.S. National Library of Medicine, Aug. 22, 2016 NCT02071862.
Chen et al., "Targeting glutamine induces apoptosis: a cancer therapy approach," Int J Mol Sci, 16(9):22830-22855 (2015).
Kaufman et al., "Treatment of KRAS-Mutant Non-Small Cell Lung Cancer: The End of the Beginning for Targeted Therapies," JAMA, 18:1835-1837 (2017).
Xiang et al., "Targeted inhibition of tumor-specific glutaminase diminishes cell-autonomous tumorigenesis," J Clin Invest, 125(6):2293-2306 (2015).
Schiller et al., "Efficacy and safety of axitinib in patients with advanced non-small-cell lung cancer: results from a phase II study," J Clin Oncol, 27(23): 3836-3841 (2009).
Tanizaki et al., "MET tyrosine kinase inhibitor crizotinib (PF-02341066) shows differential antitumor effects in non-small cell lung cancer according to MET alterations," J Thorac Oncol, 6(10):1624-1631 (2011).
Filipp et al., "Glutamine-fueled mitochondrial metabolism is decoupled from glycolysis in melanoma," Pigment Cell Melanoma Res, 25:732-739 (2012).
Son et al., "Glutamine supports pancreatic cancer growth through a KRAS-regulated metabolic pathway," Nature, 496:101-105 (2013).
van den Heuvel et al., "Analysis of glutamine dependency in non-small cell lung cancer: GLS1 splice variant GAC is essential for cancer cell growth," Cancer Biol Ther, 13(12):1185-94 (2012).
Gameiro et al., "In Vivo HIF-Mediated Reductive Carboxylation Is Regulated by Citrate Levels and Sensitizes VHL-Deficient Cells to Glutamine Deprivation," Cell Metabolism, 17:372 (2013).
Gao et al., "c-Myc suppression of miR-23a/b enhances mitochondrial glutaminase expression and glutamine metabolism," Nature, 458(7239):762-5 (2009).

\* cited by examiner

COMBINATION THERAPY WITH GLUTAMINASE INHIBITORS AND IMMUNO-ONCOLOGY AGENTS

RELATED APPLICATIONS

This application claims the benefit of priority to U.S. Provisional Patent Application No. 62/237,287, filed Oct. 5, 2015 and U.S. Provisional Patent Application No. 62/323,179, filed Apr. 15, 2016, which applications are hereby incorporated by reference in their entirety.

BACKGROUND

Cancer is characterized by the uncontrolled growth of cells in the body, leading to the invasion of essential organs and often death. Initially, the pharmacological treatment of cancer utilized non-specific cytotoxic agents that targeted all rapidly dividing cells, including normal cells. These non-specific cytotoxic agents have anti-tumor effects but their use is often limited by severe toxicities. As the understanding of the proteins and pathways that enable cancer cells to thrive has evolved, newer more targeted agents have been developed that block specific proteins that are activated in cancer cells. However, the interplay between these pathways is complex and poorly understood even after years of research.

Therefore, there is a need to develop new ways of treating cancer.

SUMMARY OF INVENTION

The present invention provides methods of treating or preventing cancer, an immunological disease, or a chronic infection, comprising conjointly administering a glutaminase inhibitor and an immuno-oncology therapeutic agent.

In some embodiments, the immuno-oncology therapeutic agent is an inhibitor of arginase, CTLA-4, indoleamine 2,3-dioxygenase, and/or PD-1/PD-L1. In certain embodiments, the immuno-oncology agent is abagovomab, adecatumumab, afutuzumab, alemtuzumab, anatumomab mafenatox, apolizumab, blinatumomab, BMS-936559, catumaxomab, durvalumab, epacadostat, epratuzumab, indoximod, inotuzumab ozogamicin, intelumumab, ipilimumab, isatuximab, lambrolizumab, MED14736, MPDL3280A, nivolumab, obinutuzumab, ocaratuzumab, ofatumumab, olatatumab, pembrolizumab, pidilizumab, rituximab, ticilimumab, samalizumab, or tremelimumab. In some embodiments, the immuno-oncology agent is indoximod, ipilimumab, nivolumab, pembrolizumab, or pidilizumab.

In certain embodiments, the glutaminase inhibitor is a compound of formula I,

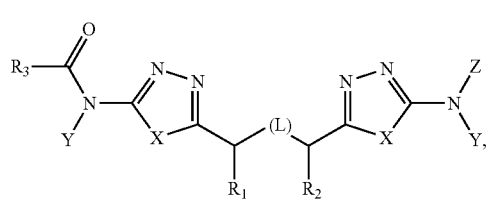

(I)

or a pharmaceutically acceptable salt thereof, wherein:
L represents $CH_2SCH_2$, $CH_2CH_2$, $CH_2CH_2CH_2$, $CH_2$, $CH_2S$, $SCH_2$, $CH_2NHCH_2$, $CH=CH$, or

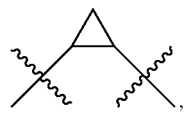 [SMILES: *C1CC1*]

preferably $CH_2CH_2$, wherein any hydrogen atom of a CH or $CH_2$ unit may be replaced by alkyl or alkoxy, any hydrogen of an NH unit may be replaced by alkyl, and any hydrogen atom of a $CH_2$ unit of $CH_2CH_2$, $CH_2CH_2CH_2$ or $CH_2$ may be replaced by hydroxy;

X, independently for each occurrence, represents S, O or $CH=CH$, preferably S or $CH=CH$, wherein any hydrogen atom of a CH unit may be replaced by alkyl;

Y, independently for each occurrence, represents H or $CH_2O(CO)R_7$ $R_7$, independently for each occurrence, represents H or substituted or unsubstituted alkyl, alkoxy, aminoalkyl, alkylaminoalkyl, heterocyclylalkyl, arylalkyl, or heterocyclylalkoxy;

Z represents H or $R_3(CO)$;

$R_1$ and $R_2$ each independently represent H, alkyl, alkoxy or hydroxy;

$R_3$, independently for each occurrence, represents substituted or unsubstituted alkyl, hydroxyalkyl, aminoalkyl, acylaminoalkyl, alkenyl, alkoxy, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, heteroaryloxyalkyl or $C(R_8)(R_9)(R_{10})$, $N(R_4)(R_5)$ or $OR_6$, wherein any free hydroxyl group may be acylated to form $C(O)R_7$;

$R_4$ and $R_5$ each independently represent H or substituted or unsubstituted alkyl, hydroxyalkyl, acyl, aminoalkyl, acylaminoalkyl, alkenyl, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, or heteroaryloxyalkyl, wherein any free hydroxyl group may be acylated to form $C(O)R_7$;

$R_6$, independently for each occurrence, represents substituted or unsubstituted alkyl, hydroxyalkyl, aminoalkyl, acylaminoalkyl, alkenyl, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, or heteroaryloxyalkyl, wherein any free hydroxyl group may be acylated to form $C(O)R_7$; and $R_8$, $R_9$ and $R_{10}$ each independently represent H or substituted or unsubstituted alkyl, hydroxy, hydroxyalkyl, amino, acylamino, aminoalkyl, acylaminoalkyl, alkoxycarbonyl, alkoxycarbonylamino, alkenyl, alkoxy, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, or heteroaryloxyalkyl, or $R_8$ and $R_9$ together with the carbon to which they are attached, form a carbocyclic or heterocyclic ring system, wherein any free hydroxyl group may be acylated to form $C(O)R_7$, and wherein at least two of $R_8$, $R_9$ and $R_{10}$ are not H.

In certain embodiments, the cancer is selected from bladder cancer, breast cancer (including TNBC), cervical cancer, colorectal cancer, chronic lymphocytic leukemia (CLL), diffuse large B-cell lymphoma (DLBCL), esophageal adenocarcinoma, glioblastoma, head and neck cancer, leukemia (acute and chronic), low-grade glioma, lung cancer (including adenocarcinoma, non-small cell lung cancer, and squamous cell carcinoma), Hodgkin's lymphoma, non-Hodgkin lymphoma (NHL), melanoma, multiple myeloma (MM), ovarian cancer, pancreatic cancer, prostate cancer, renal cancer (including renal clear cell carcinoma and kidney papillary cell carcinoma), and stomach cancer.

In certain embodiments, the immunological disease is selected from ankylosing spondylitis, Crohn's disease, erythema nodosum leprosum (ENL), graft versus host disease (GVHD), HIV-associated wasting syndrome, lupus erythematosus, organ transplant rejection, post-polycythemia, psoriasis, psoriatic arthritis, recurrent aphthous ulcers, rheumatoid arthritis (RA), severe recurrent aphthous stomatitis, systemic sclerosis, and tuberous sclerosis.

In certain embodiments, the chronic infection is selected from bladder infection, chronic fatigue syndrome, cytomegalovirus/epstein barr virus, fibromyalgia, hepatitis B virus (HBV), hepatitis C virus (HCV), HIV/AIDS virus, mycoplasma infection, and urinary tract infections.

In certain embodiments, the present invention provides a pharmaceutical preparation suitable for use in a human patient in the treatment or prevention of cancer, immunological diseases, or chronic infection, comprising an effective amount of a glutaminase inhibitor (such as a compound of formula I), an immuno-oncology therapeutic agent, and one or more pharmaceutically acceptable excipients. In certain embodiments, the pharmaceutical preparations may be for use in treating or preventing a condition or disease as described herein.

In other embodiments, the present invention provides a kit for the treatment or prevention of cancer, an immunological disease, or a chronic infection, comprising an effective amount of an immuno-oncology therapeutic agent and an effective amount of a glutaminase inhibitor (such as a compound of formula I), wherein the immuno-oncology therapeutic agent and glutaminase inhibitor are optionally formulated as pharmaceutical compositions, either separately or in combination. In certain embodiments, the kits may be for use in treating or preventing a condition or disease as described herein.

DETAILED DESCRIPTION OF THE INVENTION

Figure 1:
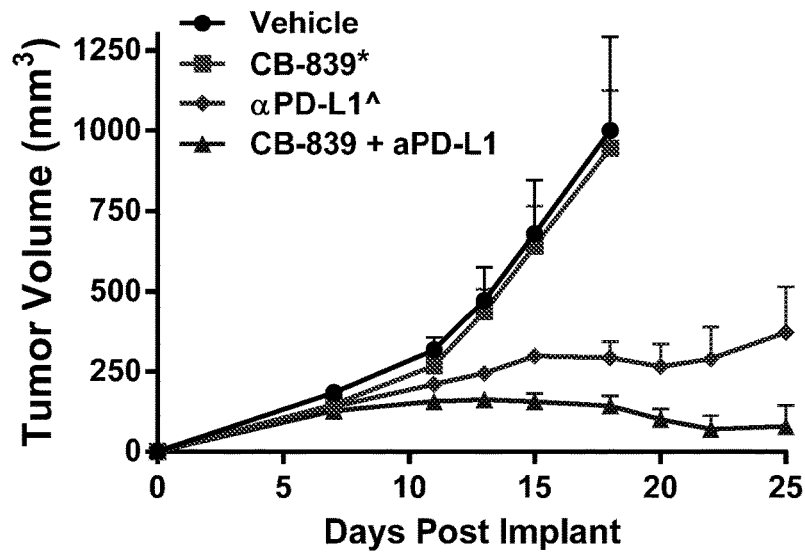
FIG. 1 is a graph showing the changes in tumor volume over time in female balb/c mice implanted with colon carcinoma cells. Four treatment groups are shown (vehicle, CB-839, anti-PD-L1 antibody, and combination CB-839 and anti-PD-L1 antibody). The mean plus or minus the standard error from n=10 animals is plotted.

The present invention provides a method of treating or preventing cancer, an immunological disease, or a chronic infection comprising conjointly administering a glutaminase inhibitor and an immuno-oncology therapeutic agent.

In certain embodiments, conjointly administering the immuno-oncology therapeutic agent and glutaminase inhibitor provides improved efficacy relative to individual administration of the immuno-oncology therapeutic agent or glutaminase inhibitor as a single agent.

In certain embodiments, the conjoint administration of the immuno-oncology therapeutic agent and glutaminase inhibitor provides an additive effect.

In certain embodiments, the conjoint administration of the immuno-oncology therapeutic agent and glutaminase inhibitor provides a synergistic effect.

In certain embodiments, the immuno-oncology therapeutic agent and glutaminase inhibitor are administered simultaneously.

In certain embodiments, the immuno-oncology therapeutic agent is administered within about 5 minutes to within about 168 hours prior or after of the glutaminase inhibitor.

In some embodiments, the immuno-oncology therapeutic agent is an inhibitor of CTLA-4, indoleamine 2,3-dioxygenase, and/or PD-1/PD-L1.

In certain embodiments, the immuno-oncology therapeutic agent is an inhibitor of arginase, CTLA-4, or PD-1/PD-L1. In certain embodiments, the immuno-oncology therapeutic agent is an inhibitor of PD-L1. In certain embodiments, the immuno-oncology agent is an anti-PD-L1 antibody.

In certain embodiments, the immuno-oncology agent is abagovomab, adecatumumab, afutuzumab, alemtuzumab, anatumomab mafenatox, apolizumab, atezolimab, avelumab, blinatumomab, BMS-936559, catumaxomab, durvalumab, epacadostat, epratuzumab, indoximod, inotuzumab ozogamicin, intelumumab, ipilimumab, isatuximab, lambrolizumab, MED14736, MPDL3280A, nivolumab, obinutuzumab, ocaratuzumab, ofatumumab, olatatumab, pembrolizumab, pidilizumab, rituximab, ticilimumab, samalizumab, or tremelimumab.

In certain embodiments, the immuno-oncology agent is abagovomab, adecatumumab, afutuzumab, alemtuzumab, anatumomab mafenatox, apolizumab, blinatumomab, BMS-936559, catumaxomab, durvalumab, epacadostat, epratuzumab, indoximod, inotuzumab ozogamicin, intelumumab, ipilimumab, isatuximab, lambrolizumab, MED14736, MPDL3280A, nivolumab, obinutuzumab, ocaratuzumab, ofatumumab, olatatumab, pembrolizumab, pidilizumab, rituximab, ticilimumab, samalizumab, or tremelimumab.

In some embodiments, the immuno-oncology agent is indoximod, ipilimumab, nivolumab, pembrolizumab, or pidilizumab.

In certain embodiments, the immuno-oncology agent is ipilimumab.

In certain embodiments, the glutaminase inhibitor is a compound of formula I,

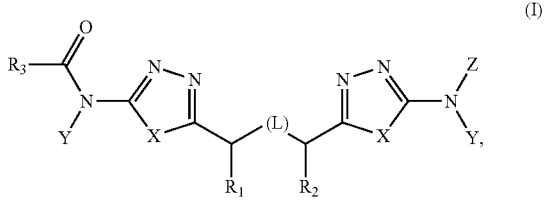

or a pharmaceutically acceptable salt thereof, wherein:
L represents $CH_2SCH_2$, $CH_2CH_2$, $CH_2CH_2CH_2$, $CH_2$, $CH_2S$, $SCH_2$, $CH_2NHCH_2$, $CH=CH$, or

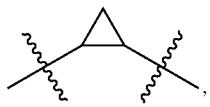 [SMILES: *C1CC1*]

preferably $CH_2CH_2$, wherein any hydrogen atom of a CH or $CH_2$ unit may be replaced by alkyl or alkoxy, any hydrogen of an NH unit may be replaced by alkyl, and any hydrogen atom of a $CH_2$ unit of $CH_2CH_2$, $CH_2CH_2CH_2$ or $CH_2$ may be replaced by hydroxy;

X, independently for each occurrence, represents S, O or $CH=CH$, preferably S or $CH=CH$, wherein any hydrogen atom of a CH unit may be replaced by alkyl;

Y, independently for each occurrence, represents H or $CH_2O(CO)R_7$ $R_7$, independently for each occurrence, represents H or substituted or unsubstituted alkyl, alkoxy, aminoalkyl, alkylaminoalkyl, heterocyclylalkyl, arylalkyl, or heterocyclylalkoxy;

Z represents H or $R_3(CO)$;

$R_1$ and $R_2$ each independently represent H, alkyl, alkoxy or hydroxy;

$R_3$, independently for each occurrence, represents substituted or unsubstituted alkyl, hydroxyalkyl, aminoalkyl, acylaminoalkyl, alkenyl, alkoxy, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, heteroaryloxyalkyl or $C(R_8)(R_9)(R_{10})$, $N(R_4)(R_5)$ or $OR_6$, wherein any free hydroxyl group may be acylated to form $C(O)R_7$;

$R_4$ and $R_5$ each independently represent H or substituted or unsubstituted alkyl, hydroxyalkyl, acyl, aminoalkyl, acylaminoalkyl, alkenyl, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, or heteroaryloxyalkyl, wherein any free hydroxyl group may be acylated to form $C(O)R_7$;

$R_6$, independently for each occurrence, represents substituted or unsubstituted alkyl, hydroxyalkyl, aminoalkyl, acylaminoalkyl, alkenyl, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, or heteroaryloxyalkyl, wherein any free hydroxyl group may be acylated to form $C(O)R_7$; and $R_8$, $R_9$ and $R_{10}$ each independently represent H or substituted or unsubstituted alkyl, hydroxy, hydroxyalkyl, amino, acylamino, aminoalkyl, acylaminoalkyl, alkoxycarbonyl, alkoxycarbonylamino, alkenyl, alkoxy, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, or heteroaryloxyalkyl, or $R_8$ and $R_9$ together with the carbon to which they are attached, form a carbocyclic or heterocyclic ring system, wherein any free hydroxyl group may be acylated to form $C(O)R_7$, and wherein at least two of $R_8$, $R_9$ and $R_{10}$ are not H.

In certain embodiments wherein alkyl, hydroxyalkyl, amino, acylamino, aminoalkyl, acylaminoalkyl, alkenyl, alkoxy, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, or heteroaryloxyalkyl are substituted, they are substituted with one or more substituents selected from substituted or unsubstituted alkyl, such as perfluoroalkyl (e.g., trifluoromethyl), alkenyl, alkoxy, alkoxyalkyl, aryl, aralkyl, arylalkoxy, aryloxy, aryloxyalkyl, hydroxyl, halo, alkoxy, such as perfluoroalkoxy (e.g., trifluoromethoxy), alkoxyalkoxy, hydroxyalkyl, hydroxyalkylamino, hydroxyalkoxy, amino, aminoalkyl, alkylamino, aminoalkylalkoxy, aminoalkoxy, acylamino, acylaminoalkyl, such as perfluoro acylaminoalkyl (e.g., trifluoromethylacylaminoalkyl), acyloxy, cycloalkyl, cycloalkylalkyl, cycloalkylalkoxy, heterocyclyl, heterocyclylalkyl, heterocyclyloxy, heterocyclylalkoxy, heteroaryl, heteroarylalkyl, heteroarylalkoxy, heteroaryloxy, heteroaryloxyalkyl, heterocyclylaminoalkyl, heterocyclylaminoalkoxy, amido, amidoalkyl, amidine, imine, oxo, carbonyl (such as carboxyl, alkoxycarbonyl, formyl, or acyl, including perfluoroacyl (e.g., $C(O)CF_3$)), carbonylalkyl (such as carboxyalkyl, alkoxycarbonylalkyl, formylalkyl, or acylalkyl, including perfluoroacylalkyl (e.g., -alkylC(O)CF$_3$)), carbamate, carbamatealkyl, urea, ureaalkyl, sulfate, sulfonate, sulfamoyl, sulfone, sulfonamide, sulfonamidealkyl, cyano, nitro, azido, sulfhydryl, alkylthio, thiocarbonyl (such as thioester, thioacetate, or thioformate), phosphoryl, phosphate, phosphonate or phosphinate.

In certain embodiments, L represents $CH_2SCH_2$, $CH_2CH_2$, $CH_2CH_2CH_2$, $CH_2$, $CH_2S$, $SCH_2$, or $CH_2NHCH_2$, wherein any hydrogen atom of a $CH_2$ unit may be replaced by alkyl or alkoxy, and any hydrogen atom of a $CH_2$ unit of $CH_2CH_2$, $CH_2CH_2CH_2$ or $CH_2$ may be replaced by hydroxyl. In certain embodiments, L represents $CH_2SCH_2$, $CH_2CH_2$, $CH_2S$ or $SCH_2$. In certain embodiments, L represents $CH_2CH_2$. In certain embodiments, L is not $CH_2SCH_2$.

In certain embodiments, Y represents H.

In certain embodiments, X represents S or $CH=CH$. In certain embodiments, one or both X represents $CH=CH$. In certain embodiments, each X represents S. In certain embodiments, one X represents S and the other X represents $CH=CH$.

In certain embodiments, Z represents $R_3(CO)$. In certain embodiments wherein Z is $R_3(CO)$, each occurrence of $R_3$ is not identical (e.g., the compound of formula I is not symmetrical).

In certain embodiments, $R_1$ and $R_2$ each represent H.

In certain embodiments, $R_3$ represents arylalkyl, heteroarylalkyl, cycloalkyl or heterocycloalkyl. In certain embodiments, $R_3$ represents $C(R_8)(R_9)(R_{10})$, wherein $R_8$ represents aryl, arylalkyl, heteroaryl or heteroaralkyl, such as aryl, arylalkyl or heteroaryl, $R_9$ represents H, and $R_{10}$ represents hydroxy, hydroxyalkyl, alkoxy or alkoxyalkyl, such as hydroxy, hydroxyalkyl or alkoxy.

In certain embodiments, L represents $CH_2SCH_2$, $CH_2CH_2$, $CH_2S$ or $SCH_2$, such as $CH_2CH_2$, $CH_2S$ or $SCH_2$, Y represents H, X represents S, Z represents $R_3(CO)$, $R_1$ and $R_2$ each represent H, and each $R_3$ represents arylalkyl, heteroarylalkyl, cycloalkyl or heterocycloalkyl. In certain such embodiments, each occurrence of $R_3$ is identical.

In certain embodiments, L represents $CH_2SCH_2$, $CH_2CH_2$, $CH_2S$ or $SCH_2$, Y represents H, X represents S, Z represents $R_3(CO)$, $R_1$ and $R_2$ each represent H, and each $R_3$ represents $C(R_8)(R_9)(R_{10})$, wherein $R_8$ represents aryl, arylalkyl, heteroaryl or heteroaralkyl, such as aryl, arylalkyl or heteroaryl, $R_9$ represents H, and $R_{10}$ represents hydroxy, hydroxyalkyl, alkoxy or alkoxyalkyl, such as hydroxy, hydroxyalkyl or alkoxy. In certain such embodiments, each occurrence of $R_3$ is identical.

In certain embodiments, L represents $CH_2CH_2$, Y represents H, X represents S or CH=CH, Z represents $R_3(CO)$, $R_1$ and $R_2$ each represent H, and each $R_3$ represents substituted or unsubstituted arylalkyl, heteroarylalkyl, cycloalkyl or heterocycloalkyl. In certain such embodiments, each X represents S. In other embodiments, one or both occurrences of X represents CH=CH, such as one occurrence of X represents S and the other occurrence of X represents CH=CH. In certain embodiments of the foregoing, each occurrence of $R_3$ is identical. In other embodiments of the foregoing wherein one occurrence of X represents S and the other occurrence of X represents CH=CH, the two occurrences of $R_3$ are not identical.

In certain embodiments, L represents $CH_2CH_2$, Y represents H, X represents S, Z represents $R_3(CO)$, $R_1$ and $R_2$ each represent H, and each $R_3$ represents $C(R_8)(R_9)(R_{10})$, wherein $R_8$ represents aryl, arylalkyl or heteroaryl, $R_9$ represents H, and $R_{10}$ represents hydroxy, hydroxyalkyl or alkoxy. In certain such embodiments, $R_8$ represents aryl and $R_{10}$ represents hydroxyalkyl. In certain such embodiments, each occurrence of $R_3$ is identical.

In certain embodiments wherein L represents $CH_2$, $CH_2CH_2CH_2$ or $CH_2CH_2$, X represents O, and Z represents $R_3(CO)$, both $R_3$ groups are not alkyl, such as methyl, or $C(R_8)(R_9)(R_{10})$, wherein $R_8$, $R_9$ and $R_{10}$ are each independently hydrogen or alkyl.

In certain embodiments wherein L represents $CH_2CH_2$, X represents S, and Z represents $R_3(CO)$, both $R_3$ groups are not phenyl or heteroaryl, such as 2-furyl. In certain embodiments wherein L represents $CH_2CH_2$, X represents O, and Z represents $R_3(CO)$, both $R_3$ groups are not $N(R_4)(R_5)$ wherein $R_4$ is aryl, such as phenyl, and $R_5$ is H.

In certain embodiments wherein L represents $CH_2SCH_2$, X represents S, and Z represents $R_3(CO)$, both $R_3$ groups are not aryl, such as optionally substituted phenyl, aralkyl, such as benzyl, heteroaryl, such as 2-furyl, 2-thienyl or 1,2,4-trizole, substituted or unsubstituted alkyl, such as methyl, chloromethyl, dichloromethyl, n-propyl, n-butyl, t-butyl or hexyl, heterocyclyl, such as pyrimidine-2,4(1H,3H)-dione, or alkoxy, such as methoxy, pentyloxy or ethoxy.

In certain embodiments wherein L represents $CH_2SCH_2$, X represents S, and Z represents $R_3(CO)$, both $R_3$ groups are not $N(R_4)(R_5)$ wherein $R_4$ is aryl, such as substituted or unsubstituted phenyl (e.g., phenyl, 3-tolyl, 4-tolyl, 4-bromophenyl or 4-nitrophenyl), and $R_5$ is H.

In certain embodiments wherein L represents $CH_2CH_2CH_2$, X represents S, and Z represents $R_3(CO)$, both $R_3$ groups are not alkyl, such as methyl, ethyl, or propyl, cycloalkyl, such as cyclohexyl, or $C(R_8)(R_9)(R_{10})$, wherein any of $R_8$, $R_9$ and $R_{10}$ together with the C to which they are attached, form any of the foregoing.

In certain embodiments of the methods described herein, the glutaminase inhibitor is a compound of formula Ia,

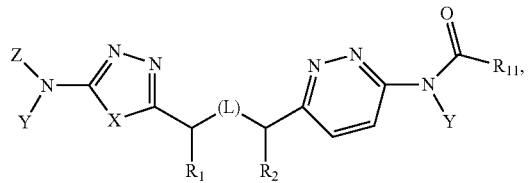

(Ia)

or a pharmaceutically acceptable salt thereof, wherein:

L represents $CH_2SCH_2$, $CH_2CH_2$, $CH_2CH_2CH_2$, $CH_2$, $CH_2S$, $SCH_2$, $CH_2NHCH_2$, CH=CH, or

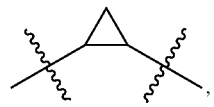 [SMILES: *C1CC1*]

preferably $CH_2CH_2$, wherein any hydrogen atom of a CH or $CH_2$ unit may be replaced by alkyl or alkoxy, any hydrogen of an NH unit may be replaced by alkyl, and any hydrogen atom of a $CH_2$ unit of $CH_2CH_2$, $CH_2CH_2CH_2$ or $CH_2$ may be replaced by hydroxy;

X represents S, O or CH=CH, preferably S or CH=CH, wherein any hydrogen atom of a CH unit may be replaced by alkyl;

Y, independently for each occurrence, represents H or $CH_2O(CO)R_7$;

$R_7$, independently for each occurrence, represents H or substituted or unsubstituted alkyl, alkoxy, aminoalkyl, alkylaminoalkyl, heterocyclylalkyl, arylalkyl, or heterocyclylalkoxy;

Z represents H or $R_3(CO)$;

$R_1$ and $R_2$ each independently represent H, alkyl, alkoxy or hydroxy, preferably H;

$R_3$ represents substituted or unsubstituted alkyl, hydroxyalkyl, aminoalkyl, acylaminoalkyl, alkenyl, alkoxy, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, heteroaryloxyalkyl or $C(R_8)(R_9)(R_{10})$, $N(R_4)(R_5)$ or $OR_6$, wherein any free hydroxyl group may be acylated to form $C(O)R_7$;

$R_4$ and $R_5$ each independently represent H or substituted or unsubstituted alkyl, hydroxyalkyl, acyl, aminoalkyl, acylaminoalkyl, alkenyl, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, or heteroaryloxyalkyl, wherein any free hydroxyl group may be acylated to form $C(O)R_7$;

$R_6$, independently for each occurrence, represents substituted or unsubstituted alkyl, hydroxyalkyl, aminoalkyl, acylaminoalkyl, alkenyl, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, or heteroaryloxyalkyl, wherein any free hydroxyl group may be acylated to form $C(O)R_7$; and $R_8$, $R_9$ and $R_{10}$ each independently represent H or substituted or unsubstituted alkyl, hydroxy, hydroxyalkyl, amino, acylamino, aminoalkyl, acylaminoalkyl, alkoxycarbonyl, alkoxycarbonylamino, alkenyl, alkoxy, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, or heteroaryloxyalkyl, or $R_8$ and $R_9$ together with the carbon to which they are attached, form a carbocyclic or heterocyclic ring system, wherein any free hydroxyl group may be acylated to form $C(O)R_7$, and wherein at least two of $R_8$, $R_9$ and $R_{10}$ are not H;

$R_{11}$ represents substituted or unsubstituted aryl, arylalkyl, aryloxy, aryloxyalkyl, heteroaryl, heteroarylalkyl, heteroaryloxy, or heteroaryloxyalkyl, or $C(R_{12})(R_{13})(R_{14})$, $N(R_4)(R_{14})$ or $OR_{14}$, wherein any free hydroxyl group may be acylated to form $C(O)R_7$;

$R_{12}$ and $R_{13}$ each independently represent H or substituted or unsubstituted alkyl, hydroxy, hydroxyalkyl, amino, acylamino, aminoalkyl, acylaminoalkyl, alkoxycarbonyl, alkoxycarbonylamino, alkenyl, alkoxy, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, or heteroaryloxyalkyl, wherein any free hydroxyl group may be acylated to form $C(O)R_7$, and wherein both of $R_{12}$ and $R_{13}$ are not H; and $R_{14}$ represents substituted or unsubstituted aryl, arylalkyl, aryloxy, aryloxyalkyl, heteroaryl, heteroarylalkyl, heteroaryloxy, or heteroaryloxyalkyl.

In certain embodiments wherein alkyl, hydroxyalkyl, amino, acylamino, aminoalkyl, acylaminoalkyl, alkenyl, alkoxy, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, or heteroaryloxyalkyl are substituted, they are substituted with one or more substituents selected from substituted or unsubstituted alkyl, such as perfluoroalkyl (e.g., trifluoromethyl), alkenyl, alkoxy, alkoxyalkyl, aryl, aralkyl, arylalkoxy, aryloxy, aryloxyalkyl, hydroxyl, halo, alkoxy, such as perfluoroalkoxy (e.g., trifluoromethylalkoxy), alkoxyalkoxy, hydroxyalkyl, hydroxyalkylamino, hydroxyalkoxy, amino, aminoalkyl, alkylamino, aminoalkylalkoxy, aminoalkoxy, acylamino, acylaminoalkyl, such as perfluoro acylaminoalkyl (e.g., trifluoromethylacylaminoalkyl), acyloxy, cycloalkyl, cycloalkylalkyl, cycloalkylalkoxy, heterocyclyl, heterocyclylalkyl, heterocyclyloxy, heterocyclylalkoxy, heteroaryl, heteroarylalkyl, heteroarylalkoxy, heteroaryloxy, heteroaryloxyalkyl, heterocyclylaminoalkyl, heterocyclylaminoalkoxy, amido, amidoalkyl, amidine, imine, oxo, carbonyl (such as carboxyl, alkoxycarbonyl, formyl, or acyl, including perfluoroacyl (e.g., $C(O)CF_3$)), carbonylalkyl (such as carboxyalkyl, alkoxycarbonylalkyl, formylalkyl, or acylalkyl, including perfluoroacylalkyl (e.g., -alkyl$C(O)CF_3$)), carbamate, carbamatealkyl, urea, ureaalkyl, sulfate, sulfonate, sulfamoyl, sulfone, sulfonamide, sulfonamidealkyl, cyano, nitro, azido, sulfhydryl, alkylthio, thiocarbonyl (such as thioester, thioacetate, or thioformate), phosphoryl, phosphate, phosphonate or phosphinate.

In certain embodiments, $R_{11}$ represents substituted or unsubstituted arylalkyl, such as substituted or unsubstituted benzyl.

In certain embodiments, L represents $CH_2SCH_2$, $CH_2CH_2$, $CH_2CH_2CH_2$, $CH_2$, $CH_2S$, $SCH_2$, or $CH_2NHCH_2$, wherein any hydrogen atom of a $CH_2$ unit may be replaced by alkyl or alkoxy, and any hydrogen atom of a $CH_2$ unit of $CH_2CH_2$, $CH_2CH_2CH_2$ or $CH_2$ may be replaced by hydroxyl. In certain embodiments, L represents $CH_2SCH_2$, $CH_2CH_2$, $CH_2S$ or $SCH_2$, preferably $CH_2CH_2$. In certain embodiments, L is not $CH_2SCH_2$.

In certain embodiments, each Y represents H. In other embodiments, at least one Y is $CH_2O(CO)R_7$.

In certain embodiments, X represents S or CH=CH. In certain embodiments, X represents S.

In certain embodiments, $R_1$ and $R_2$ each represent H.

In certain embodiments, Z represents $R_3(CO)$. In certain embodiments wherein Z is $R_3(CO)$, $R_3$ and $R_{11}$ are not identical (e.g., the compound of formula I is not symmetrical).

In certain embodiments, Z represents $R_3(CO)$ and $R_3$ represents arylalkyl, heteroarylalkyl, cycloalkyl or heterocycloalkyl. In certain embodiments, Z represents $R_3(CO)$ and $R_3$ represents $C(R_8)(R_9)(R_{10})$, wherein $R_8$ represents aryl, arylalkyl, heteroaryl or heteroaralkyl, such as aryl, arylalkyl or heteroaryl, $R_9$ represents H, and $R_{10}$ represents hydroxy, hydroxyalkyl, alkoxy or alkoxyalkyl, such as hydroxy, hydroxyalkyl or alkoxy. In certain embodiments, Z represents $R_3(CO)$ and $R_3$ represents heteroarylalkyl.

In certain embodiments, L represents $CH_2SCH_2$, $CH_2CH_2$, $CH_2S$ or $SCH_2$, such as $CH_2CH_2$, Y represents H, X represents S, Z represents $R_3(CO)$, $R_1$ and $R_2$ each represent H, $R_3$ represents arylalkyl, heteroarylalkyl, cycloalkyl or heterocycloalkyl, and $R_{11}$ represents arylalkyl. In certain such embodiments, $R_3$ represents heteroarylalkyl.

In certain embodiments, L represents $CH_2SCH_2$, $CH_2CH_2$, $CH_2S$ or $SCH_2$, such as $CH_2CH_2$, Y represents H, X represents S, Z represents $R_3(CO)$, $R_1$ and $R_2$ each represent H, and $R_3$ represents $C(R_8)(R_9)(R_{10})$, wherein $R_8$ represents aryl, arylalkyl, heteroaryl or heteroaralkyl, such as aryl, arylalkyl or heteroaryl, $R_9$ represents H, and $R_{10}$ represents hydroxy, hydroxyalkyl, alkoxy or alkoxyalkyl, such as hydroxy, hydroxyalkyl or alkoxy, and $R_{11}$ represents arylalkyl. In certain such embodiments, $R_8$ represents heteroaryl.

In certain embodiments, L represents $CH_2CH_2$, Y represents H, X represents S or CH=CH, such as S, Z represents $R_3(CO)$, $R_1$ and $R_2$ each represent H, $R_3$ represents substituted or unsubstituted arylalkyl, heteroarylalkyl, cycloalkyl or heterocycloalkyl, and $R_{11}$ represents arylalkyl. In certain such embodiments, $R_3$ represents heteroarylalkyl.

In certain embodiments, L represents $CH_2CH_2$, Y represents H, X represents S, Z represents $R_3(CO)$, $R_1$ and $R_2$ each represent H, $R_3$ represents $C(R_8)(R_9)(R_{10})$, wherein $R_8$ represents aryl, arylalkyl or heteroaryl, $R_9$ represents H, and $R_{10}$ represents hydroxy, hydroxyalkyl or alkoxy, and $R_{11}$ represents arylalkyl. In certain such embodiments, $R_8$ represents aryl and $R_{10}$ represents hydroxyalkyl. In certain other embodiments, $R_8$ represents heteroaryl.

In certain embodiments of the methods described herein, the glutaminase inhibitor is a compound having the structure of Formula (II):

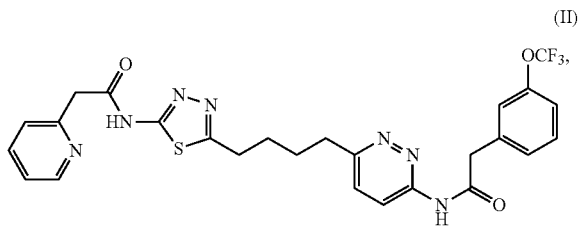 [SMILES: O=C(Cc1cccc(OC(F)(F)F)c1)Nc1ccc(CCCCc2nnc(NC(=O)Cc3ccccn3)s2)nn1]

(II)

or a pharmaceutically acceptable salt thereof. The compound of Formula (II) is alternatively referred to herein as "CB-839."

In certain embodiments, the cancer is Acute Lymphoblastic Leukemia (ALL), Acute Myeloid Leukemia (AML), Adrenocortical Carcinoma, Anal Cancer, Appendix Cancer, Atypical Teratoid/Rhabdoid Tumor, Basal Cell Carcinoma, Bile Duct Cancer, Bladder Cancer, Bone Cancer, Brain Tumor, Astrocytoma, Brain and Spinal Cord Tumor, Brain Stem Glioma, Central Nervous System Atypical Teratoid/ Rhabdoid Tumor, Central Nervous System Embryonal Tumors, Breast Cancer, Bronchial Tumors, Burkitt Lymphoma, Carcinoid Tumor, Carcinoma of Unknown Primary, Central Nervous System Cancer, Cervical Cancer, Childhood Cancers, Chordoma, Chronic Lymphocytic Leukemia (CLL), Chronic Myelogenous Leukemia (CML), Chronic Myeloproliferative Disorders, Colon Cancer, Colorectal Cancer, Craniopharyngioma, Cutaneous T-Cell Lymphoma, Ductal Carcinoma In Situ (DCIS), Embryonal Tumors, Endometrial Cancer, Ependymoblastoma, Ependymoma, Esophageal Cancer, Esthesioneuroblastoma, Ewing Sarcoma, Extracranial Germ Cell Tumor, Extragonadal Germ Cell Tumor, Extrahepatic Bile Duct Cancer, Eye Cancer, Fibrous Histiocytoma of Bone, Gallbladder Cancer, Gastric Cancer, Gastrointestinal Carcinoid Tumor, Gastrointestinal Stromal Tumors (GIST), Germ Cell Tumor, Ovarian Germ Cell Tumor, Gestational Trophoblastic Tumor, Glioma, Hairy Cell Leukemia, Head and Neck Cancer, Heart Cancer, Hepatocellular Cancer, Histiocytosis, Langerhans Cell Cancer, Hodgkin Lymphoma, Hypopharyngeal Cancer, Intraocular Melanoma, Islet Cell Tumors, Kaposi Sarcoma, Kidney Cancer, Langerhans Cell Histiocytosis, Laryngeal Cancer, Leukemia, Lip and Oral Cavity Cancer, Liver Cancer, Lobular Carcinoma In Situ (LCIS), Lung Cancer, Lymphoma, AIDS-Related Lymphoma, Macroglobulinemia, Male Breast Cancer, Medulloblastoma, Medulloepithelioma, Melanoma, Merkel Cell Carcinoma, Malignant Mesothelioma, Metastatic Squamous Neck Cancer with Occult Primary, Midline Tract Carcinoma Involving NUT Gene, Mouth Cancer, Multiple Endocrine Neoplasia Syndrome, Multiple Myeloma/Plasma Cell Neoplasm, Mycosis Fungoides, Myelodysplastic Syndrome, Myelodysplastic/ Myeloproliferative Neoplasm, Chronic Myelogenous Leukemia (CML), Acute Myeloid Leukemia (AML), Myeloma, Multiple Myeloma, Chronic Myeloproliferative Disorder, Nasal Cavity Cancer, Paranasal Sinus Cancer, Nasopharyngeal Cancer, Neuroblastoma, Non-Hodgkin Lymphoma, Non-Small Cell Lung Cancer, Oral Cancer, Oral Cavity Cancer, Lip Cancer, Oropharyngeal Cancer, Osteosarcoma, Ovarian Cancer, Pancreatic Cancer, Papillomatosis, Paraganglioma, Paranasal Sinus Cancer, Nasal Cavity Cancer, Parathyroid Cancer, Penile Cancer, Pharyngeal Cancer, Pheochromocytoma, Pineal Parenchymal Tumors of Intermediate Differentiation, Pineoblastoma, Pituitary Tumor, Plasma Cell Neoplasm, Pleuropulmonary Blastoma, Breast Cancer, Primary Central Nervous System (CNS) Lymphoma, Prostate Cancer, Rectal Cancer, Renal Cell Cancer, Clear cell renal cell carcinoma, Renal Pelvis Cancer, Ureter Cancer, Transitional Cell Cancer, Retinoblastoma, Rhabdomyosarcoma, Salivary Gland Cancer, Sarcoma, Sézary Syndrome, Skin Cancer, Small Cell Lung Cancer, Small Intestine Cancer, Soft Tissue Sarcoma, Squamous Cell Carcinoma, Squamous Neck Cancer with Occult Primary, Squamous Cell Carcinoma of the Head and Neck (HNSCC), Stomach Cancer, Supratentorial Primitive Neuroectodermal Tumors, T-Cell Lymphoma, Testicular Cancer, Throat Cancer, Thymoma, Thymic Carcinoma, Thyroid Cancer, Transitional Cell Cancer of the Renal Pelvis and Ureter, Triple Negative Breast Cancer (TNBC), Gestational Trophoblastic Tumor, Unknown Primary, Unusual Cancer of Childhood, Urethral Cancer, Uterine Cancer, Uterine Sarcoma, Waldenström Macroglobulinemia, or Wilms Tumor.

In certain embodiments, the cancer is selected from bladder cancer, breast cancer (including TNBC), cervical cancer, colorectal cancer, chronic lymphocytic leukemia (CLL), diffuse large B-cell lymphoma (DLBCL), esophageal adenocarcinoma, glioblastoma, head and neck cancer, leukemia (acute and chronic), low-grade glioma, lung cancer (including adenocarcinoma, non-small cell lung cancer, and squamous cell carcinoma), Hodgkin's lymphoma, non-Hodgkin lymphoma (NHL), melanoma, multiple myeloma (MM), ovarian cancer, pancreatic cancer, prostate cancer, renal cancer (including renal clear cell carcinoma and kidney papillary cell carcinoma), and stomach cancer.

In certain embodiments, the cancer is multiple myeloma.

In certain embodiments, the cancer is renal cell carcinoma.

In certain embodiments, the cancer is non-small cell lung cancer (NSCLC).

In certain embodiments, the cancer is melanoma.

In certain embodiments, the cancer is bladder cancer.

In certain embodiments, the cancer is colon cancer.

In certain embodiments the immunological disease is selected from ankylosing spondylitis, Crohn's disease, erythema nodosum leprosum (ENL), graft versus host disease (GVHD), HIV-associated wasting syndrome, lupus erythematosus, organ transplant rejection, post-polycythemia, psoriasis, psoriatic arthritis, recurrent aphthous ulcers, rheumatoid arthritis (RA), severe recurrent aphthous stomatitis, systemic sclerosis, and tuberous sclerosis.

In certain embodiments, the chronic infection is selected from bladder infection, chronic fatigue syndrome, cytomegalovirus/epstein barr virus, fibromyalgia, hepatitis B virus (HBV), hepatitis C virus (HCV), HIV/AIDS virus, mycoplasma infection, and urinary tract infections.

In certain embodiments, the glutaminase inhibitor is selected from any one of the compounds disclosed in Table 3 of PCT Application Publication Number WO 2013/ 078123, published May 30, 2013, the contents of which are incorporated herein by reference. Preferably, the compound is selected from compound 1, 2, 6, 7, 8, 11, 13, 14, 15, 16, 17, 18, 19, 20, 21, 24, 25, 26, 27, 28, 29, 30, 31, 32, 33, 35, 36, 38, 39, 40, 41, 43, 44, 47, 48, 50, 51, 52, 54, 55, 58, 63, 64, 65, 67, 68, 69, 70, 71, 72, 73, 77, 78, 79, 80, 81, 82, 83, 84, 85, 86, 87, 88, 92, 93, 94, 95, 97, 99, 100, 102, 105, 107, 111, 112, 114, 115, 116, 117, 118, 120, 121, 122, 123, 126, 127, 133, 135, 136, 138, 140, 141, 143, 146, 147, 148, 152, 153, 155, 156, 157, 158, 159, 160, 161, 162, 163, 164, 165, 166, 168, 169, 170, 172, 173, 174, 175, 176, 177, 178, 179, 180, 181, 182, 185, 186, 187, 188, 189, 190, 193, 194, 195, 196, 197, 198, 199, 200, 201, 202, 203, 204, 205, 208, 210, 211, 213, 214, 216, 217, 219, 220, 226, 227, 228, 229, 231, 232, 234, 235, 236, 237, 239, 240, 241, 242, 243, 244, 245, 246, 247, 248, 249, 250, 251, 252, 255, 256, 257, 258, 259, 260, 261, 262, 263, 264, 265, 266, 267, 268, 269, 270, 271, 273, 274, 275, 276, 278, 279, 280, 281, 282, 283, 285, 286, 287, 288, 290, 291, 292, 293, 294, 295, 296, 297, 298, 299, 300, 302, 304, 1038, 306, 307, 308, 309, 310, 311, 313, 314, 315, 316, 317, 318, 319, 320, 321, 322, 323, 324, 325, 327, 329, 332, 333, 334, 335, 336, 337, 338, 339, 340, 341, 342, 343, 344, 345, 346, 527, 347, 348, 349, 350, 351, 352, 353, 354, 355, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 638, 639, 640, 641, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 692, 693, 694, 695, 696, 697, 698, 699, 700, 701, 702, 703, 704, 705, 707, 708, 709, 715, 716, 717, 718, 719, 720, 721, 722, 723, 724, 725, 726, 727, 728, 729, or 730.

In certain embodiments, the glutaminase inhibitor may be a prodrug of a compound of formula I or Ia, e.g., wherein a hydroxyl in the parent compound is presented as an ester or a carbonate, or carboxylic acid present in the parent compound is presented as an ester. In certain such embodiments, the prodrug is metabolized to the active parent compound in vivo (e.g., the ester is hydrolyzed to the corresponding hydroxyl or carboxylic acid).

In certain embodiments, glutaminase inhibitor compounds may be racemic. In certain embodiments, glutaminase inhibitor compounds may be enriched in one enantiomer. For example, a glutaminase inhibitor may have greater than 30% ee, 40% ee, 50% ee, 60% ee, 70% ee, 80% ee, 90% ee, or even 95% or greater ee. In certain embodiments, glutaminase inhibitors may have more than one stereocenter. In certain such embodiments, the inhibitors may be enriched in one or more diastereomer. For example, an inhibitor may have greater than 30% de, 40% de, 50% de, 60% de, 70% de, 80% de, 90% de, or even 95% or greater de.

In certain embodiments, the present invention relates to methods of treating or preventing cancer, such as bladder cancer, breast cancer (including TNBC), cervical cancer, colorectal cancer, chronic lymphocytic leukemia (CLL), diffuse large B-cell lymphoma (DLBCL), esophageal adenocarcinoma, glioblastoma, head and neck cancer, leukemia (acute and chronic), low-grade glioma, lung cancer (including adenocarcinoma, non-small cell lung cancer, and squamous cell carcinoma), Hodgkin's lymphoma, non-Hodgkin lymphoma (NHL), melanoma, multiple myeloma (MM), ovarian cancer, pancreatic cancer, prostate cancer, renal cancer (including renal clear cell carcinoma and kidney papillary cell carcinoma), or stomach cancer, with an immuno-oncology agent, such as abagovomab, adecatumumab, afutuzumab, alemtuzumab, anatumomab mafenatox, apolizumab, atezolimab, avelumab, blinatumomab, BMS-936559, catumaxomab, durvalumab, epacadostat, epratuzumab, indoximod, inotuzumab ozogamicin, intelumumab, ipilimumab, isatuximab, lambrolizumab, MED14736, MPDL3280A, nivolumab, obinutuzumab, ocaratuzumab, ofatumumab, olatatumab, pembrolizumab, pidilizumab, rituximab, ticilimumab, samalizumab, or tremelimumab, and a glutaminase inhibitor, such as a compound of formula I, Ia, II, or a pharmaceutically acceptable salt thereof.

In certain such embodiments, the immuno-oncology agent is abagovomab, adecatumumab, afutuzumab, alemtuzumab, anatumomab mafenatox, apolizumab, blinatumomab, BMS-936559, catumaxomab, durvalumab, epacadostat, epratuzumab, indoximod, inotuzumab ozogamicin, intelumumab, ipilimumab, isatuximab, lambrolizumab, MED14736, MPDL3280A, nivolumab, obinutuzumab, ocaratuzumab, ofatumumab, olatatumab, pembrolizumab, pidilizumab, rituximab, ticilimumab, samalizumab, or tremelimumab.

In certain embodiments, the present invention relates to methods of treating or preventing cancer with an immuno-oncology agent such an anti-CTLA-4 antibody (e.g., ipilimumab) or a anti-PD-L1 antibody and a glutaminase inhibitor, such as a compound of formula I, Ia, II, or a pharmaceutically acceptable salt thereof.

In certain exemplary embodiments, the present invention provides methods of treating cancer with a glutaminase inhibitor, e.g., CB-839, in combination with an anti-PD-L1 antibody as the immuno-oncology agent. In certain such embodiments, the cancer is renal cell carcinoma. In certain such embodiments, the combination of CB-839 and anti-PD-L1 antibody in cancer therapies provides a synergistic effect.

In certain embodiments, the present invention relates to methods of treating or preventing immunological disease, such as ankylosing spondylitis, Crohn's disease, erythema nodosum leprosum (ENL), graft versus host disease (GVHD), HIV-associated wasting syndrome, lupus erythematosus, organ transplant rejection, post-polycythemia, psoriasis, psoriatic arthritis, recurrent aphthous ulcers, rheumatoid arthritis (RA), severe recurrent aphthous stomatitis, systemic sclerosis, and tuberous sclerosis, with an immuno-oncology agent, such as abagovomab, adecatumumab, afutuzumab, alemtuzumab, anatumomab mafenatox, apolizumab, blinatumomab, BMS-936559, catumaxomab, durvalumab, epacadostat, epratuzumab, indoximod, inotuzumab ozogamicin, intelumumab, ipilimumab, isatuximab, lambrolizumab, MED14736, MPDL3280A, nivolumab, obinutuzumab, ocaratuzumab, ofatumumab, olatatumab, pembrolizumab, pidilizumab, rituximab, ticilimumab, samalizumab, or tremelimumab, and a glutaminase inhibitor, such as a compound of formula I, Ia, II, or a pharmaceutically acceptable salt thereof. In certain embodiments, the methods of treating or preventing an immunological disease comprise administration of an immuno-oncology agent, an anti-CTLA-4 antibody (e.g., ipilimumab) or a anti-PD-L1 antibody, and a glutaminase inhibitor, such as a compound of formula I, Ia, II, or a pharmaceutically acceptable salt thereof.

In certain embodiments, the present invention relates to methods of treating or preventing a chronic infection, such as bladder infection, chronic fatigue syndrome, cytomegalovirus/epstein barr virus, fibromyalgia, hepatitis B virus (HBV), hepatitis C virus (HCV), HIV/AIDS virus, mycoplasma infection, or urinary tract infections, with an immuno-oncology agent, such as abagovomab, adecatumumab, afutuzumab, alemtuzumab, anatumomab mafenatox, apolizumab, blinatumomab, BMS-936559, catumaxomab, durvalumab, epacadostat, epratuzumab, indoximod, inotuzumab ozogamicin, intelumumab, ipilimumab, isatuximab, lambrolizumab, MED14736, MPDL3280A, nivolumab, obinutuzumab, ocaratuzumab, ofatumumab, olatatumab, pembrolizumab, pidilizumab, rituximab, ticilimumab, samalizumab, or tremelimumab, and a glutaminase inhibitor, such as a compound of formula I, Ia, II, or a pharmaceutically acceptable salt thereof. In certain embodiments, the methods of treating or preventing a chronic infection comprise administration of an immuno-oncology agent, such as an anti-CTLA-4 antibody (e.g., ipilimumab)

or a anti-PD-L1 antibody, and a glutaminase inhibitor, such as a compound of formula I, Ia, II, or a pharmaceutically acceptable salt thereof.

In certain embodiments, the present invention provides a pharmaceutical composition comprising an immuno-oncology agent, such as abagovomab, adecatumumab, afutuzumab, alemtuzumab, anatumomab mafenatox, apolizumab, atezolimab, avelumab, blinatumomab, BMS-936559, catumaxomab, durvalumab, epacadostat, epratuzumab, indoximod, inotuzumab ozogamicin, intelumumab, ipilimumab, isatuximab, lambrolizumab, MED14736, MPDL3280A, nivolumab, obinutuzumab, ocaratuzumab, ofatumumab, olatatumab, pembrolizumab, pidilizumab, rituximab, ticilimumab, samalizumab, or tremelimumab, and a glutaminase inhibitor, such as a compound of formula I, Ia, II, or a pharmaceutically acceptable salt thereof.

In certain such embodiments, the immuno-oncology agent is abagovomab, adecatumumab, afutuzumab, alemtuzumab, anatumomab mafenatox, apolizumab, blinatumomab, BMS-936559, catumaxomab, durvalumab, epacadostat, epratuzumab, indoximod, inotuzumab ozogamicin, intelumumab, ipilimumab, isatuximab, lambrolizumab, MED14736, MPDL3280A, nivolumab, obinutuzumab, ocaratuzumab, ofatumumab, olatatumab, pembrolizumab, pidilizumab, rituximab, ticilimumab, samalizumab, or tremelimumab.

In certain embodiments, the present invention provides a pharmaceutical composition comprising an immuno-oncology agent, such as an anti-CTLA-4 antibody (e.g., ipilimumab) or a anti-PD-L1 antibody, and a glutaminase inhibitor, such as a compound of formula I, Ia, II, or a pharmaceutically acceptable salt thereof.

In certain embodiments, the therapeutic preparation of the glutaminase inhibitor may be enriched to provide predominantly one enantiomer of a compound (e.g., of formula I or Ia). An enantiomerically enriched mixture may comprise, for example, at least 60 mol percent of one enantiomer, or more preferably at least 75, 90, 95, or even 99 mol percent. In certain embodiments, the glutaminase inhibitor compound enriched in one enantiomer is substantially free of the other enantiomer, wherein substantially free means that the substance in question makes up less than 10%, or less than 5%, or less than 4%, or less than 3%, or less than 2%, or less than 1% as compared to the amount of the other enantiomer, e.g., in the composition or compound mixture. For example, if a glutaminase inhibitor composition or compound mixture contains 98 grams of a first enantiomer and 2 grams of a second enantiomer, it would be said to contain 98 mol percent of the first enantiomer and only 2% of the second enantiomer.

In certain embodiments, the therapeutic preparation may be enriched to provide predominantly one diastereomer of a glutaminase inhibitor compound (e.g., of formula I or Ia). A diastereomerically enriched mixture may comprise, for example, at least 60 mol percent of one diastereomer, or more preferably at least 75, 90, 95, or even 99 mol percent.

In certain embodiments, the present invention provides a pharmaceutical preparation suitable for use in a human patient, comprising an immuno-oncology agent selected from inhibitors of CTLA-4, indoleamine 2,3-dioxygenase, and PD-1/PD-L1 and any of the compounds shown above (e.g., a glutaminase inhibitor, such as a compound of formula I, Ia, or II), and one or more pharmaceutically acceptable excipients. In certain embodiments, the pharmaceutical preparations may be for use in treating or preventing a condition or disease as described herein. In certain embodiments, the pharmaceutical preparations have a low enough pyrogen activity to be suitable for use in a human patient.

One embodiment of the present invention provides a pharmaceutical kit comprising an immuno-oncology agent, such as abagovomab, adecatumumab, afutuzumab, alemtuzumab, anatumomab mafenatox, apolizumab, atezolimab, avelumab, blinatumomab, BMS-936559, catumaxomab, durvalumab, epacadostat, epratuzumab, indoximod, inotuzumab ozogamicin, intelumumab, ipilimumab, isatuximab, lambrolizumab, MED14736, MPDL3280A, nivolumab, obinutuzumab, ocaratuzumab, ofatumumab, olatatumab, pembrolizumab, pidilizumab, rituximab, ticilimumab, samalizumab, or tremelimumab, and a glutaminase inhibitor, such as a compound of formula I, Ia, II, or a pharmaceutically acceptable salt thereof, and directions on how to administer the immuno-oncology agent and glutaminase inhibitor.

In other embodiments, the present invention provides a pharmaceutical kit comprising an immuno-oncology agent, such as an anti-CTLA-4 antibody (e.g., ipilimumab) or a anti-PD-L1 antibody, and a glutaminase inhibitor, such as a compound of formula I, Ia, II, or a pharmaceutically acceptable salt thereof, and directions on how to administer the immuno-oncology agent and glutaminase inhibitor.

Uses of the Invention

Combination therapy is an important treatment modality in many disease settings, such as cancer. Recent scientific advances have increased our understanding of the pathophysiological processes that underlie these and other complex diseases. This increased understanding has provides impetus to develop new therapeutic approaches using combinations of drugs directed at multiple therapeutic targets to improve treatment response, minimize development of resistance, or minimize adverse events. In settings in which combination therapy provides significant therapeutic advantages, there is growing interest in the development of combinations with new investigational drugs, such as glutaminase inhibitors.

Although interest in combination therapy, sometimes referred to as polytherapy, has been most prominent in oncology, it also has potential application in other therapeutic settings such as immunological diseases.

When considering the administration of multiple therapeutic agents together, one must be concerned about what sort of drug interactions will be observed. This action can be positive (when the drug's effect is increased) or antagonistic (when the drug's effect is decreased) or a new side effect can be produced that neither produces on its own.

When the interaction causes an increase in the effects of one or both of the drugs the interaction, the degree to which the final effect of the combined drugs is greater than administering either drug alone can be calculated resulting in what is called the "combination index" (CI) (Chou and Talalay, 1984). A combination index at or around 1 is considered "additive"; whereas a value greater than 1 is considered "synergistic".

Immune-targeted agents (also known as immuno-oncology agents) act against tumors by modulating immune cells. The field of cancer immunotherapy is rapidly growing, with new targets constantly being identified (Chen and Mellman, 2013; Morrissey et al., 2016; Kohrt et al., 2016). The present invention provides a combination of an immuno-oncology agent and a glutaminase inhibitor.

Examples of immuno-oncology agents comprise agents that modulate immune checkpoints such as 2B4, 4-1BB (CD137), AaR, B7-H3, B7-H4, BAFFR, BTLA, CD2, CD7, CD27, CD28, CD30, CD40, CD80, CD83 ligand, CD86, CD160, CD200, CDS, CEACAM, CTLA-4, GITR, HVEM, ICAM-1, KIR, LAG-3, LAIR1, LFA-1 (CD11a/CD18), LIGHT, NKG2C, NKp80, OX40, PD-1, PD-L1, PD-L2, SLAMF7, TGFRβ, TIGIT, Tim3 and VISTA.

Immuno-oncology agents may be in the form of antibodies, peptides, small molecules or viruses.

The present invention provides a combination therapy comprising an immuno-oncology agent selected from inhibitors of CTLA-4, indoleamine 2,3-dioxygenase, and PD-1/PD-L1, and a glutaminase inhibitor. In certain embodiments, the combination therapy treats or prevents cancer, an immunological disorder, or a chronic infection.

Certain embodiments of the invention relate to treating cancer comprising administering an immuno-oncology agent and a glutaminase inhibitor. In certain embodiments, the cancer may be one or a variant of a cancer selected from Acute Lymphoblastic Leukemia (ALL), Acute Myeloid Leukemia (AML), Adrenocortical Carcinoma, Anal Cancer, Appendix Cancer, Atypical Teratoid/Rhabdoid Tumor, Basal Cell Carcinoma, Bile Duct Cancer, Bladder Cancer, Bone Cancer, Brain Tumor, Astrocytoma, Brain and Spinal Cord Tumor, Brain Stem Glioma, Central Nervous System Atypical Teratoid/Rhabdoid Tumor, Central Nervous System Embryonal Tumors, Breast Cancer, Bronchial Tumors, Burkitt Lymphoma, Carcinoid Tumor, Carcinoma of Unknown Primary, Central Nervous System Cancer, Cervical Cancer, Childhood Cancers, Chordoma, Chronic Lymphocytic Leukemia (CLL), Chronic Myelogenous Leukemia (CML), Chronic Myeloproliferative Disorders, Colon Cancer, Colorectal Cancer, Craniopharyngioma, Cutaneous T-Cell Lymphoma Ductal Carcinoma In Situ (DCIS), Embryonal Tumors, Endometrial Cancer, Ependymoblastoma, Ependymoma, Esophageal Cancer, Esthesioneuroblastoma, Ewing Sarcoma, Extracranial Germ Cell Tumor, Extragonadal Germ Cell Tumor, Extrahepatic Bile Duct Cancer, Eye Cancer, Fibrous Histiocytoma of Bone, Gallbladder Cancer, Gastric Cancer, Gastrointestinal Carcinoid Tumor, Gastrointestinal Stromal Tumors (GIST), Germ Cell Tumor, Extracranial Germ Cell Tumor, Extragonadal Germ Cell Tumor, Ovarian Germ Cell Tumor, Gestational Trophoblastic Tumor, Glioma, Hairy Cell Leukemia, Head and Neck Cancer, Heart Cancer, Hepatocellular Cancer, Histiocytosis, Langerhans Cell Cancer, Hodgkin Lymphoma, Hypopharyngeal Cancer, Intraocular Melanoma, Islet Cell Tumors, Kaposi Sarcoma, Kidney Cancer, Langerhans Cell Histiocytosis, Laryngeal Cancer, Leukemia, Lip and Oral Cavity Cancer, Liver Cancer, Lobular Carcinoma In Situ (LCIS), Lung Cancer, Lymphoma, AIDS-Related Lymphoma, Macroglobulinemia, Male Breast Cancer, Medulloblastoma, Medulloepithelioma, Melanoma, Merkel Cell Carcinoma, Malignant Mesothelioma, Metastatic Squamous Neck Cancer with Occult Primary, Midline Tract Carcinoma Involving NUT Gene, Mouth Cancer, Multiple Endocrine Neoplasia Syndrome, Multiple Myeloma/Plasma Cell Neoplasm, Mycosis Fungoides, Myelodysplastic Syndrome, Myelodysplastic/Myeloproliferative Neoplasm, Chronic Myelogenous Leukemia (CML), Acute Myeloid Leukemia (AML), Myeloma, Multiple Myeloma, Chronic Myeloproliferative Disorder, Nasal Cavity Cancer, Paranasal Sinus Cancer, Nasopharyngeal Cancer, Neuroblastoma, Non-Hodgkin Lymphoma, Non-Small Cell Lung Cancer, Oral Cancer, Oral Cavity Cancer, Lip Cancer, Oropharyngeal Cancer, Osteosarcoma, Ovarian Cancer, Pancreatic Cancer, Papillomatosis, Paraganglioma, Paranasal Sinus Cancer, Nasal Cavity Cancer, Parathyroid Cancer, Penile Cancer, Pharyngeal Cancer, Pheochromocytoma, Pineal Parenchymal Tumors of Intermediate Differentiation, Pineoblastoma, Pituitary Tumor, Plasma Cell Neoplasm, Pleuropulmonary Blastoma, Breast Cancer, Primary Central Nervous System (CNS) Lymphoma, Prostate Cancer, Rectal Cancer, Renal Cell Cancer, Clear cell renal cell carcinoma, Renal Pelvis Cancer, Ureter Cancer, Transitional Cell Cancer, Retinoblastoma, Rhabdomyosarcoma, Salivary Gland Cancer, Sarcoma, Sézary Syndrome, Skin Cancer, Small Cell Lung Cancer, Small Intestine Cancer, Soft Tissue Sarcoma, Squamous Cell Carcinoma, Squamous Neck Cancer with Occult Primary (e.g., Metastatic), Squamous Cell Carcinoma of the Head and Neck (HNSCC), Stomach Cancer, Supratentorial Primitive Neuroectodermal Tumors, T-Cell Lymphoma, Testicular Cancer, Throat Cancer, Thymoma, Thymic Carcinoma, Thyroid Cancer, Transitional Cell Cancer of the Renal Pelvis and Ureter, Triple Negative Breast Cancer (TNBC), Gestational Trophoblastic Tumor, Unknown Primary, Unusual Cancer of Childhood, Urethral Cancer, Uterine Cancer, Uterine Sarcoma, Waldenström Macroglobulinemia, and Wilms Tumor.

In certain embodiments the cancer is selected from bladder cancer, breast cancer (including TNBC), cervical cancer, colorectal cancer, chronic lymphocytic leukemia (CLL), diffuse large B-cell lymphoma (DLBCL), esophageal adenocarcinoma, glioblastoma, head and neck cancer, leukemia (acute and chronic), low-grade glioma, lung cancer (including adenocarcinoma, non-small cell lung cancer, and squamous cell carcinoma), Hodgkin's lymphoma, non-Hodgkin lymphoma (NHL), melanoma, multiple myeloma (MM), ovarian cancer, pancreatic cancer, prostate cancer, renal cancer (including renal clear cell carcinoma and kidney papillary cell carcinoma), and stomach cancer.

Diseases involving the immune system (referred to as immunological, immune-mediated or immune-related disorders/diseases) are caused by abnormally low activity or overactivity of the immune system. In cases of immune system overactivity, the body attacks and damages its own tissues (also known as autoimmune disease). Although not all-inclusive, some known immune-related disorders include ankylosing spondylitis, Crohn's disease, erythema nodosum leprosum (ENL), graft versus host disease (GVHD), HIV-associated wasting syndrome, lupus erythematosus, organ transplant rejection, post-polycythemia, psoriasis, psoriatic arthritis, recurrent aphthous ulcers, rheumatoid arthritis (RA), severe recurrent aphthous stomatitis, systemic sclerosis, and tuberous sclerosis. In certain embodiments, the invention provides for the method of treating an immunological disease comprising administering an immuno-oncology agent and a glutaminase inhibitor. In certain embodiments the immune-mediated disorder is selected from ankylosing spondylitis, Crohn's disease, erythema nodosum leprosum (ENL), graft versus host disease (GVHD), HIV-associated wasting syndrome, lupus erythematosus, organ transplant rejection, post-polycythemia, psoriasis, psoriatic arthritis, recurrent aphthous ulcers, rheumatoid arthritis (RA), severe recurrent aphthous stomatitis, systemic sclerosis, and tuberous sclerosis.

Glutamine plays an important role as a carrier of nitrogen, carbon, and energy. It is used for hepatic urea synthesis, for renal ammoniagenesis, for gluconeogenesis, and as respiratory fuel for many cells. The conversion of glutamine into glutamate is initiated by the mitochondrial enzyme, glutaminase ("GLS"). There are two major forms of the enzyme, K-type and L-type, which are distinguished by their Km values for glutamine and response to glutamate, wherein the Km value, or Michaelis constant, is the concentration of substrate required to reach half the maximal velocity. The L-type, also known as "liver-type" or GLS2, has a high Km for glutamine and is glutamate resistant. The K-type, also known as "kidney-type or GLS1, has a low Km for glutamine and is inhibited by glutamate. An alternative splice form of GLS1, referred to as glutaminase C or "GAC", has been identified recently and has similar activity characteristics of GLS1. In certain embodiments, the glutaminase inhibitor compounds may selectively inhibit GLS1, GLS2 and GAC. In a preferred embodiment, the glutaminase inhibitor compounds selectively inhibit GLS1 and GAC.

In certain embodiments, the method of treating or preventing cancer, immunological disease, or chronic infection may further comprise administering one or more additional therapeutic agents conjointly with the immuno-oncology agent and glutaminase inhibitor. Therapeutic agents that may be conjointly administered with compounds of the invention include: aminoglutethimide, amsacrine, anastrozole, asparaginase, AZD5363, Bacillus Calmette-Guérin vaccine (bcg), bicalutamide, bleomycin, bortezomib, buserelin, busulfan, campothecin, capecitabine, carboplatin, carfilzomib, carmustine, chlorambucil, chloroquine, cisplatin, cladribine, clodronate, cobimetinib, colchicine, cyclophosphamide, cyproterone, cytarabine, dacarbazine, dactinomycin, daunorubicin, demethoxyviridin, dexamethasone, dichloroacetate, dienestrol, diethylstilbestrol, docetaxel, doxorubicin, epirubicin, erlotinib, estradiol, estramustine, etoposide, everolimus, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, lenalidomide, letrozole, leucovorin, leuprolide, levami sole, lomustine, lonidamine, mechlorethamine, medroxyprogesterone, megestrol, melphalan, mercaptopurine, mesna, metformin, methotrexate, miltefosine, mitomycin, mitotane, mitoxantrone, MK-2206, nilutamide, nocodazole, octreotide, olaparib, oxaliplatin, paclitaxel, pamidronate, pazopanib, pentostatin, perifosine, plicamycin, pomalidomide, porfimer, procarbazine, raltitrexed, rituximab, rucaparib, selumetinib, sorafenib, streptozocin, sunitinib, suramin, talazoparib, tamoxifen, temozolomide, temsirolimus, teniposide, testosterone, thalidomide, thioguanine, thiotepa, titanocene dichloride, topotecan, trametinib, trastuzumab, tretinoin, veliparib, vinblastine, vincristine, vindesine, and vinorelbine.

Many combination therapies have been developed for the treatment of cancer. In certain embodiments, compounds of the invention may be conjointly administered with a combination therapy. Examples of combination therapies with which compounds of the invention may be conjointly administered are included in Table 1.

TABLE 1

Exemplary combinatorial therapies for the treatment of cancer.

| Name | Therapeutic agents |
|---|---|
| ABV | Doxorubicin, Bleomycin, Vinblastine |
| ABVD | Doxorubicin, Bleomycin, Vinblastine, Dacarbazine |
| AC (Breast) | Doxorubicin, Cyclophosphamide |
| AC (Sarcoma) | Doxorubicin, Cisplatin |
| AC (Neuroblastoma) | Cyclophosphamide, Doxorubicin |
| ACE | Cyclophosphamide, Doxorubicin, Etoposide |
| ACe | Cyclophosphamide, Doxorubicin |
| AD | Doxorubicin, Dacarbazine |
| AP | Doxorubicin, Cisplatin |
| ARAC-DNR | Cytarabine, Daunorubicin |
| B-CAVe | Bleomycin, Lomustine, Doxorubicin, Vinblastine |
| BCVPP | Carmustine, Cyclophosphamide, Vinblastine, Procarbazine, Prednisone |
| BEACOPP | Bleomycin, Etoposide, Doxorubicin, Cyclophosphamide, Vincristine, Procarbazine, Prednisone, Filgrastim |
| BEP | Bleomycin, Etoposide, Cisplatin |
| BIP | Bleomycin, Cisplatin, Ifosfamide, Mesna |
| BOMP | Bleomycin, Vincristine, Cisplatin, Mitomycin |
| CA | Cytarabine, Asparaginase |
| CABO | Cisplatin, Methotrexate, Bleomycin, Vincristine |
| CAF | Cyclophosphamide, Doxorubicin, Fluorouracil |
| CAL-G | Cyclophosphamide, Daunorubicin, Vincristine, Prednisone, Asparaginase |
| CAMP | Cyclophosphamide, Doxorubicin, Methotrexate, Procarbazine |
| CAP | Cyclophosphamide, Doxorubicin, Cisplatin |
| CaT | Carboplatin, Paclitaxel |
| CAV | Cyclophosphamide, Doxorubicin, Vincristine |
| CAVE ADD | CAV and Etoposide |
| CA-VP16 | Cyclophosphamide, Doxorubicin, Etoposide |
| CC | Cyclophosphamide, Carboplatin |
| CDDP/VP-16 | Cisplatin, Etoposide |
| CEF | Cyclophosphamide, Epirubicin, Fluorouracil |
| CEPP(B) | Cyclophosphamide, Etoposide, Prednisone, with or without/Bleomycin |
| CEV | Cyclophosphamide, Etoposide, Vincristine |
| CF | Cisplatin, Fluorouracil or Carboplatin Fluorouracil |
| CHAP | Cyclophosphamide or Cyclophosphamide, Altretamine, Doxorubicin, Cisplatin |
| ChlVPP | Chlorambucil, Vinblastine, Procarbazine, Prednisone |
| CHOP | Cyclophosphamide, Doxorubicin, Vincristine, Prednisone |
| CHOP-BLEO | Add Bleomycin to CHOP |
| CISCA | Cyclophosphamide, Doxorubicin, Cisplatin |
| CLD-BOMP | Bleomycin, Cisplatin, Vincristine, Mitomycin |
| CMF | Methotrexate, Fluorouracil, Cyclophosphamide |
| CMFP | Cyclophosphamide, Methotrexate, Fluorouracil, Prednisone |
| CMFVP | Cyclophosphamide, Methotrexate, Fluorouracil, Vincristine, Prednisone |
| CMV | Cisplatin, Methotrexate, Vinblastine |
| CNF | Cyclophosphamide, Mitoxantrone, Fluorouracil |
| CNOP | Cyclophosphamide, Mitoxantrone, Vincristine, Prednisone |
| COB | Cisplatin, Vincristine, Bleomycin |
| CODE | Cisplatin, Vincristine, Doxorubicin, Etoposide |
| COMLA | Cyclophosphamide, Vincristine, Methotrexate, Leucovorin, Cytarabine |
| COMP | Cyclophosphamide, Vincristine, Methotrexate, Prednisone |
| Cooper Regimen | Cyclophosphamide, Methotrexate, Fluorouracil, Vincristine, Prednisone |
| COP | Cyclophosphamide, Vincristine, Prednisone |
| COPE | Cyclophosphamide, Vincristine, Cisplatin, Etoposide |
| COPP | Cyclophosphamide, Vincristine, Procarbazine, Prednisone |
| CP(Chronic lymphocytic leukemia) | Chlorambucil, Prednisone |
| CP (Ovarian Cancer) | Cyclophosphamide, Cisplatin |
| CT | Cisplatin, Paclitaxel |
| CVD | Cisplatin, Vinblastine, Dacarbazine |
| CVI | Carboplatin, Etoposide, Ifosfamide, Mesna |
| CVP | Cyclophosphamide, Vincristine, Prednisome |
| CVPP | Lomustine, Procarbazine, Prednisone |
| CYVADIC | Cyclophosphamide, Vincristine, Doxorubicin, Dacarbazine |
| DA | Daunorubicin, Cytarabine |
| DAT | Daunorubicin, Cytarabine, Thioguanine |
| DAV | Daunorubicin, Cytarabine, Etoposide |
| DCT | Daunorubicin, Cytarabine, Thioguanine |
| DHAP | Cisplatin, Cytarabine, Dexamethasone |
| DI | Doxorubicin, Ifosfamide |
| DTIC/ Tamoxifen | Dacarbazine, Tamoxifen |
| DVP | Daunorubicin, Vincristine, Prednisone |
| EAP | Etoposide, Doxorubicin, Cisplatin |
| EC | Etoposide, Carboplatin |
| EFP | Etoposie, Fluorouracil, Cisplatin |

TABLE 1-continued

Exemplary combinatorial therapies for the treatment of cancer.

| Name | Therapeutic agents |
|---|---|
| ELF | Etoposide, Leucovorin, Fluorouracil |
| EMA 86 | Mitoxantrone, Etoposide, Cytarabine |
| EP | Etoposide, Cisplatin |
| EVA | Etoposide, Vinblastine |
| FAC | Fluorouracil, Doxorubicin, Cyclophosphamide |
| FAM | Fluorouracil, Doxorubicin, Mitomycin |
| FAMTX | Methotrexate, Leucovorin, Doxorubicin |
| FAP | Fluorouracil, Doxorubicin, Cisplatin |
| F-CL | Fluorouracil, Leucovorin |
| FEC | Fluorouracil, Cyclophosphamide, Epirubicin |
| FED | Fluorouracil, Etoposide, Cisplatin |
| FL | Flutamide, Leuprolide |
| FZ | Flutamide, Goserelin acetate implant |
| HDMTX | Methotrexate, Leucovorin |
| Hexa-CAF | Altretamine, Cyclophosphamide, Methotrexate, Fluorouracil |
| ICE-T | Ifosfamide, Carboplatin, Etoposide, Paclitaxel, Mesna |
| IDMTX/6-MP | Methotrexate, Mercaptopurine, Leucovorin |
| IE | Ifosfamide, Etoposie, Mesna |
| IfoVP | Ifosfamide, Etoposide, Mesna |
| IPA | Ifosfamide, Cisplatin, Doxorubicin |
| M-2 | Vincristine, Carmustine, Cyclophosphamide, Prednisone, Melphalan |
| MAC-III | Methotrexate, Leucovorin, Dactinomycin, Cyclophosphamide |
| MACC | Methotrexate, Doxorubicin, Cyclophosphamide, Lomustine |
| MACOP-B | Methotrexate, Leucovorin, Doxorubicin, Cyclophosphamide, Vincristine, Bleomycin, Prednisone |
| MAID | Mesna, Doxorubicin, Ifosfamide, Dacarbazine |
| m-BACOD | Bleomycin, Doxorubicin, Cyclophosphamide, Vincristine, Dexamethasone, Methotrexate, Leucovorin |
| MBC | Methotrexate, Bleomycin, Cisplatin |
| MC | Mitoxantrone, Cytarabine |
| MF | Methotrexate, Fluorouracil, Leucovorin |
| MICE | Ifosfamide, Carboplatin, Etoposide, Mesna |
| MINE | Mesna, Ifosfamide, Mitoxantrone, Etoposide |
| mini-BEAM | Carmustine, Etoposide, Cytarabine, Melphalan |
| MOBP | Bleomycin, Vincristine, Cisplatin, Mitomycin |
| MOP | Mechlorethamine, Vincristine, Procarbazine |
| MOPP | Mechlorethamine, Vincristine, Procarbazine, Prednisone |
| MOPP/ABV | Mechlorethamine, Vincristine, Procarbazine, Prednisone, Doxorubicin, Bleomycin, Vinblastine |
| MP (multiple myeloma) | Melphalan, Prednisone |
| MP (prostate cancer) | Mitoxantrone, Prednisone |
| MTX/6-MO | Methotrexate, Mercaptopurine |
| MTX/6-MP/VP | Methotrexate, Mercaptopurine, Vincristine, Prednisone |
| MTX-CDDPAdr | Methotrexate, Leucovorin, Cisplatin, Doxorubicin |
| MV (breast cancer) | Mitomycin, Vinblastine |
| MV (acute myelocytic leukemia) | Mitoxantrone, Etoposide |
| M-VAC Methotrexate | Vinblastine, Doxorubicin, Cisplatin |
| MVP Mitomycin | Vinblastine, Cisplatin |
| MVPP | Mechlorethamine, Vinblastine, Procarbazine, Prednisone |
| NFL | Mitoxantrone, Fluorouracil, Leucovorin |
| NOVP | Mitoxantrone, Vinblastine, Vincristine |
| OPA | Vincristine, Prednisone, Doxorubicin |
| OPPA | Add Procarbazine to OPA. |
| PAC | Cisplatin, Doxorubicin |
| PAC-I | Cisplatin, Doxorubicin, Cyclophosphamide |
| PA-CI | Cisplatin, Doxorubicin |
| PC | Paclitaxel, Carboplatin or Paclitaxel, Cisplatin |
| PCV | Lomustine, Procarbazine, Vincristine |
| PE | Paclitaxel, Estramustine |
| PFL | Cisplatin, Fluorouracil, Leucovorin |
| POC | Prednisone, Vincristine, Lomustine |
| ProMACE | Prednisone, Methotrexate, Leucovorin, Doxorubicin, Cyclophosphamide, Etoposide |
| ProMACE/cytaBOM | Prednisone, Doxorubicin, Cyclophosphamide, Etoposide, Cytarabine, Bleomycin, Vincristine, Methotrexate, Leucovorin, Cotrimoxazole |
| PRoMACE/MOPP | Prednisone, Doxorubicin, Cyclophosphamide, Etoposide, Mechlorethamine, Vincristine, Procarbazine, Methotrexate, Leucovorin |
| Pt/VM | Cisplatin, Teniposide |
| PVA | Prednisone, Vincristine, Asparaginase |
| PVB | Cisplatin, Vinblastine, Bleomycin |
| PVDA | Prednisone, Vincristine, Daunorubicin, Asparaginase |
| SMF | Streptozocin, Mitomycin, Fluorouracil |
| TAD | Mechlorethamine, Doxorubicin, Vinblastine, Vincristine, Bleomycin, Etoposide, Prednisone |
| TCF | Paclitaxel, Cisplatin, Fluorouracil |
| TIP | Paclitaxel, Ifosfamide, Mesna, Cisplatin |
| TTT | Methotrexate, Cytarabine, Hydrocortisone |
| Topo/CTX | Cyclophosphamide, Topotecan, Mesna |
| VAB-6 | Cyclophosphamide, Dactinomycin, Vinblastine, Cisplatin, Bleomycin |
| VAC | Vincristine, Dactinomycin, Cyclophosphamide |
| VACAdr | Vincristine, Cyclophosphamide, Doxorubicin, Dactinomycin, Vincristine |
| VAD | Vincristine, Doxorubicin, Dexamethasone |
| VATH | Vinblastine, Doxorubicin, Thiotepa, Flouxymesterone |
| VBAP | Vincristine, Carmustine, Doxorubicin, Prednisone |
| VBCMP | Vincristine, Carmustine, Melphalan, Cyclophosphamide, Prednisone |
| VC | Vinorelbine, Cisplatin |
| VCAP | Vincristine, Cyclophosphamide, Doxorubicin, Prednisone |
| VD | Vinorelbine, Doxorubicin |
| VelP | Vinblastine, Cisplatin, Ifosfamide, Mesna |
| VIP | Etoposide, Cisplatin, Ifosfamide, Mesna |
| VM | Mitomycin, Vinblastine |
| VMCP | Vincristine, Melphalan, Cyclophosphamide, Prednisone |
| VP | Etoposide, Cisplatin |
| V-TAD | Etoposide, Thioguanine, Daunorubicin, Cytarabine |
| 5 + 2 | Cytarabine, Daunorubicin, Mitoxantrone |
| 7 + 3 | Cytarabine with/, Daunorubicin or Idarubicin or Mitoxantrone |
| "8 in 1" | Methylprednisolone, Vincristine, Lomustine, Procarbazine, Hydroxyurea, Cisplatin, Cytarabine, Dacarbazine |

In certain embodiments of the methods of the invention described herein, the one or more additional therapeutic agents is selected from arginase inhibitors, microtubule assembly inhibitors, AKT inhibitors, mTOR inhibitors, MEK inhibitors, RTK inhibitors, ATM inhibitors, ATR inhibitors, PI3K inhibitors, EGFR inhibitors, B-Raf inhibitors, C-kit inhibitors, PARP inhibitors, DNA cross-linking agents, DNA intercalating agents, and cytidine analogs.

Cellular pathways operate more like webs than superhighways. There are multiple redundancies, or alternate routes, that may be activated in response to the inhibition of a pathway. This redundancy promotes the emergence of resistant cells or organisms under the selective pressure of a targeted agent, resulting in drug resistance and clinical relapse.

In some cases, one can overcome the resistance by the addition of another therapeutic agent. For this reason, combination therapies are often needed to effectively treat many tumors and immunological diseases.

In certain embodiments of the invention, the immuno-oncology agent is administered simultaneously with the glutaminase inhibitor. In certain embodiments, the immuno-oncology agent is administered within about 5 minutes to within about 168 hours prior or after administration of the glutaminase inhibitor. In certain embodiments, the immuno-oncology agent is administered within about 5 minutes to within about 48 hours prior or after administration of the glutaminase inhibitor. In certain embodiments, the immuno-oncology agent is administered within about 5 minutes to within about 24 hours prior or after administration of the glutaminase inhibitor.

In certain embodiments, the present invention provides a kit comprising: a) the immuno-oncology agent; b) a glutaminase inhibitor; and c) instructions for the administration of the compounds.

Definitions

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_6$ straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "$C_{x-y}$" when used in conjunction with a chemical moiety, such as, acyl, acyloxy, alkyl, alkenyl, alkynyl, or alkoxy is meant to include groups that contain from x to y carbons in the chain. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. $C_0$ alkyl indicates a hydrogen where the group is in a terminal position, a bond if internal. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkylS—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group

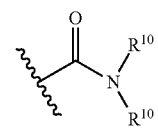

wherein each $R^{10}$ independently represent a hydrogen or hydrocarbyl group, or two $R^{10}$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

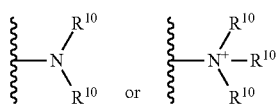

wherein each $R^{10}$ independently represents a hydrogen or a hydrocarbyl group, or two $R^{10}$ are taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

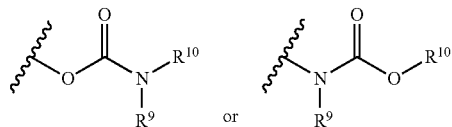

wherein $R^9$ and $R^{10}$ independently represent hydrogen or a hydrocarbyl group, such as an alkyl group, or $R^9$ and $R^{10}$ taken together with the intervening atom(s) complete a heterocycle having from 4 to 8 atoms in the ring structure.

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond. "Carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0] octane, 4,5,6,7-tetrahydro-1H-indene and bicyclo[4.1.0] hept-3-ene. "Carbocycles" may be substituted at any one or more positions capable of bearing a hydrogen atom.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds.

The term "carbocyclylalkyl", as used herein, refers to an alkyl group substituted with a carbocycle group.

The term "carbonate" is art-recognized and refers to a group —$OCO_2$—$R^{10}$, wherein $R^{10}$ represents a hydrocarbyl group.

The term "carboxy", as used herein, refers to a group represented by the formula —$CO_2H$.

The term "ester", as used herein, refers to a group —C(O)O$R^{10}$ wherein $R^{10}$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The term "heteroalkyl", as used herein, refers to a saturated or unsaturated chain of carbon atoms and at least one heteroatom, wherein no two heteroatoms are adjacent.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "heterocyclylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocyclyl, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "silyl" refers to a silicon moiety with three hydrocarbyl moieties attached thereto.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —OSO$_3$H, or a pharmaceutically acceptable salt thereof.

The term "sulfonamide" is art-recognized and refers to the group represented by the general formulae

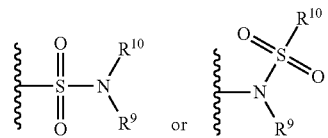

wherein R$^9$ and R$^{10}$ independently represents hydrogen or hydrocarbyl, such as alkyl, or R$^9$ and R$^{10}$ taken together with the intervening atom(s) complete a heterocycle having from 4 to 8 atoms in the ring structure.

The term "sulfoxide" is art-recognized and refers to the group —S(O)—R$^{10}$, wherein R$^{10}$ represents a hydrocarbyl.

The term "sulfonate" is art-recognized and refers to the group SO$_3$H, or a pharmaceutically acceptable salt thereof.

The term "sulfone" is art-recognized and refers to the group —S(O)$_2$—R$^{10}$, wherein R$^{10}$ represents a hydrocarbyl.

The term "thioalkyl", as used herein, refers to an alkyl group substituted with a thiol group.

The term "thioester", as used herein, refers to a group —C(O)SR$^{10}$ or —SC(O)R$^{10}$ wherein R$^{10}$ represents a hydrocarbyl.

The term "thioether", as used herein, is equivalent to an ether, wherein the oxygen is replaced with a sulfur.

The term "urea" is art-recognized and may be represented by the general formula

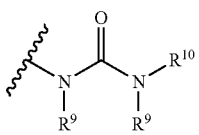

wherein R$^9$ and R$^{10}$ independently represent hydrogen or a hydrocarbyl, such as alkyl, or either occurrence of R$^9$ taken together with R$^{10}$ and the intervening atom(s) complete a heterocycle having from 4 to 8 atoms in the ring structure.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, 3$^{rd}$ Ed., 1999, John Wiley & Sons, NY and Harrison et al., *Compendium of Synthetic Organic Methods*, Vols. 1-8, 1971-1996, John Wiley & Sons, NY. Representative nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxylprotecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPS groups), glycol ethers, such as ethylene glycol and propylene glycol derivatives and allyl ethers.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

The term "prodrug" is intended to encompass compounds which, under physiologic conditions, are converted into the therapeutically active agents of the present invention (e.g., a compound of formula I). A common method for making a prodrug is to include one or more selected moieties which are hydrolyzed under physiologic conditions to reveal the desired molecule. In other embodiments, the prodrug is converted by an enzymatic activity of the host animal. For example, esters or carbonates (e.g., esters or carbonates of alcohols or carboxylic acids) are preferred prodrugs of the present invention. In certain embodiments, some or all of the compounds of formula I in a formulation represented above can be replaced with the corresponding suitable prodrug, e.g., wherein a hydroxyl in the parent compound is presented as an ester or a carbonate or carboxylic acid present in the parent compound is presented as an ester.

Pharmaceutical Compositions

The compositions and methods of the present invention may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In a preferred embodiment, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as an eye drop.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a selfemulsifying drug delivery system or a selfmicroemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for rectal, vaginal, or urethral administration may be presented as a suppository, which may be prepared by mixing one or more active compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the pharmaceutical compositions for administration to the mouth may be presented as a mouthwash, or an oral spray, or an oral ointment.

Alternatively or additionally, compositions can be formulated for delivery via a catheter, stent, wire, or other intraluminal device. Delivery via such devices may be especially useful for delivery to the bladder, urethra, ureter, rectum, or intestine.

Formulations which are suitable for vaginal administration also include pessaries, tampons, creams, gels, pastes, foams or spray formulations containing such carriers as are known in the art to be appropriate.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention. Exemplary ophthalmic formulations are described in U.S. Publication Nos. 2005/0080056, 2005/0059744, 2005/0031697 and 2005/004074 and U.S. Pat. No. 6,583,124, the contents of which are incorporated herein by reference. If desired, liquid ophthalmic formulations have properties similar to that of lacrimal fluids, aqueous humor or vitreous humor or are compatable with such fluids. A preferred route of administration is local administration (e.g., topical administration, such as eye drops, or administration via an implant).

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinacious biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

The patient receiving this treatment is any animal in need, including primates, in particular humans, and other mammals such as equines, cattle, swine and sheep; and poultry and pets in general.

In certain embodiments, compounds of the invention may be used alone or conjointly administered with another type of therapeutic agent. As used herein, the phrase "conjoint administration" refers to any form of administration of two or more different therapeutic compounds such that the second compound is administered while the previously administered therapeutic compound is still effective in the body (e.g., the two compounds are simultaneously effective in the patient, which may include synergistic effects of the two compounds). For example, the different therapeutic compounds can be administered either in the same formulation or in a separate formulation, either concomitantly or sequentially. In certain embodiments, the different therapeutic compounds can be administered within one hour, 12 hours, 24 hours, 36 hours, 48 hours, 72 hours, or a week of one another. Thus, an individual who receives such treatment can benefit from a combined effect of different therapeutic compounds.

In certain embodiments, conjoint administration of compounds of the invention with one or more additional therapeutic agent(s) (e.g., one or more additional chemotherapeutic agent(s)) provides improved efficacy relative to each individual administration of the compound of the invention (e.g., compound of formula I or Ia) or the one or more additional therapeutic agent(s). In certain such embodiments, the conjoint administration provides an additive effect, wherein an additive effect refers to the sum of each of the effects of individual administration of the compound of the invention and the one or more additional therapeutic agent(s).

This invention includes the use of pharmaceutically acceptable salts of compounds of the invention in the compositions and methods of the present invention. In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

The invention now being generally described, it will be more readily understood by reference to the following examples which are included merely for purposes of illustration of certain aspects and embodiments of the present invention, and are not intended to limit the invention.

EXAMPLE

Example 1

Figure 2:
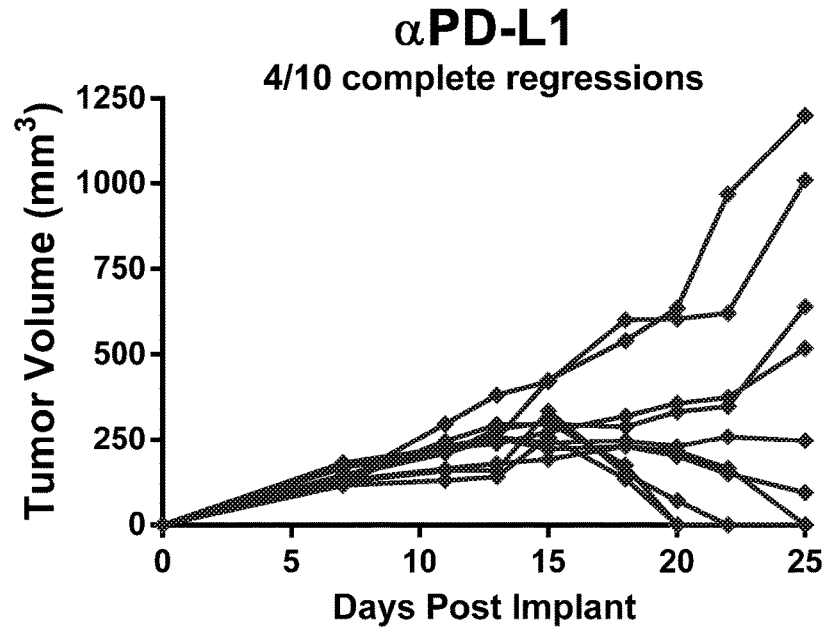
FIG. 2 is a graph showing the changes in tumor volume over time from individual mice treated with anti-PD-L1 antibody.
Figure 3:
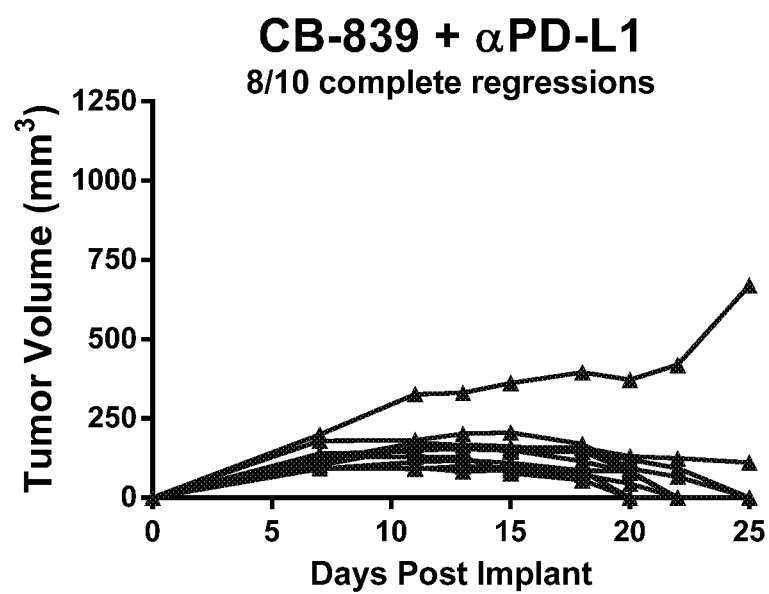
FIG. 3 is a graph showing the changes in tumor volume over time from individual mice treated with combination CB-839 and anti-PD-L1 antibody.

Female balb/c mice were implanted subcutaneously with $1 \times 10^6$ CT26 colon carcinomal cells suspended in phosphate buffered saline (PBS). Twenty-four hr post-implant, groups of n=10 mice were randomized to the following groups: 1) Vehicle control (25% Hydroxypropyl-β-cyclodextrin) dosed orally BID starting 24-hr post-implant; 2) CB-839 at 200 mg/kg (formulated at 20 mg/mL in 25% HP-β-CD) dosed orally BID starting 24-hr post-implant; 3) Anti-PD-L1 (clone 10F.9G2) at 5 mg/kg given IP on Days 5, 7, 9, 11, 13 and 15; or 4) the combination of CB-839 at 200 mg/kg PO BID plus anti-PD-L1 at 5 mg/kg given IP on Days 5, 7, 9, 11, 13 and 15. Tumors were measured with digital calipers and tumor volumes calculated using the formula tumor volume (mm$^3$)=(a×b$^2$/2) where 'a' is the largest diameter of the tumor mass and 'b' is the largest diameter perpendicular to 'a'. The mean plus or minus the standard error from n=10 animals per group are plotted in FIG. 1. In FIGS. 2 and 3, the tumor volumes from individual mice are plotted for the respective groups with the number of complete regression annotated.

Example 2

Figure 4:
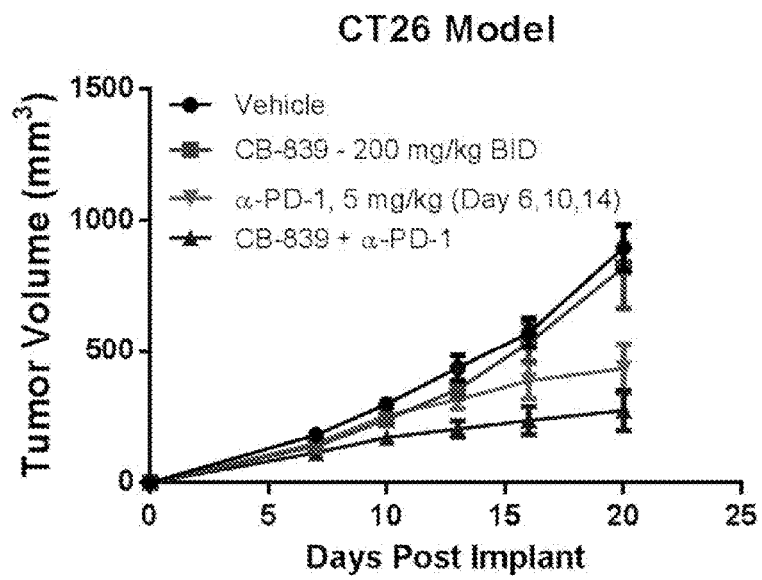
FIG. 4 is a graph showing changes in tumor volume over time in female balb/c mice implanted with colon carcinoma cells (CT26 cell line). Four treatment groups are shown (vehicle, CB-839, anti-PD-L1 antibody (αPD-1 clone RMPI-14), and combination CB-839 and anti-PD-L1 antibody). The mean plus or minus the standard error from n=10 animals is plotted.
Figure 5:
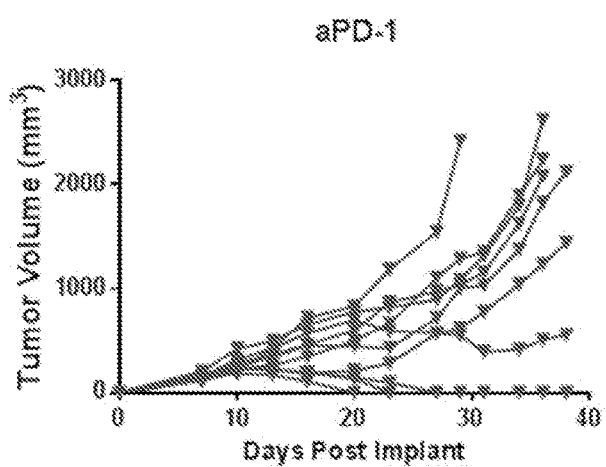
FIG. 5 is a graph showing the changes in tumor volume over time from individual mice treated with anti-PD-1 antibody.
Figure 6:
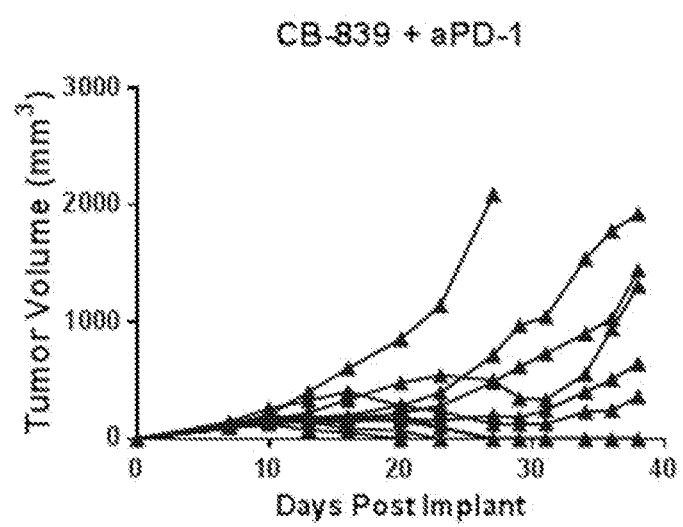
FIG. 6 is a graph showing the changes in tumor volume over time from individual mice treated with combination CB-839 and anti-PD-1 antibody.

Female balb/c mice were implanted subcutaneously with $1 \times 10^6$ CT26 colon carcinoma cells suspended in PBS. Groups of n=10 mice were treated with either 1) Vehicle (25% hydroxyl-propyl-b-cyclodextrin) orally twice daily throughout starting Day 2; 2) CB-839 dosed at 200 mg/kg orally twice daily throughout starting Day 2; 3) αPD-1 (clone RMPI-14) dosed IP at 5 mg/kg on Days 6, 10 and 14; or 4) Combination of CB-839 plus αPD-1 at their respective regimens. Tumors were measured 2-3 times per week with digital calipers and tumor volume calculated using the formula: tumor volume (mm$^3$)=(a×b$^2$/2) where 'b' is the smallest diameter and 'a' is the largest perpendicular diameter. Tumors were monitored and animals sacrificed when tumor volumes reached ≥2000 mm$^3$. FIG. 4 represents the mean+/−standard error from n=10 animals pre group through Day 20, the last day when all animals remained on study. FIGS. 5 and 6 follow the tumor volumes of individual animals on study in the αPD-1 and CB-839+αPD-1 groups.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

In particular, suitable glutaminase inhibitors for practicing the invention are described in U.S. Pat. No. 8,604,016, U.S. application Ser. No. 14/081,175, and U.S. application Ser. No. 14/095,299, which are hereby incorporated by reference herein in their entirety.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

We claim:
1. A method of therapeutically treating cancer, comprising conjointly administering a glutaminase inhibitor and an immuno-oncology therapeutic agent;
wherein the cancer is melanoma or colon cancer; and
the glutaminase inhibitor is a compound of formula (I)

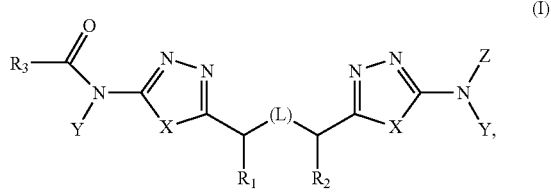

or a pharmaceutically acceptable salt thereof, wherein:
L represents CH$_2$SCH$_2$, CH$_2$CH$_2$, CH$_2$CH$_2$CH$_2$, CH$_2$, CH$_2$S, SCH$_2$, CH$_2$NHCH$_2$, CH=CH, or

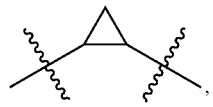 [SMILES: *C1CC1*]

wherein any hydrogen atom of a CH or CH$_2$ unit may be replaced by alkyl or alkoxy, any hydrogen of an NH unit may be replaced by alkyl, and any hydrogen atom of a CH$_2$ unit of CH$_2$CH$_2$, CH$_2$CH$_2$CH$_2$ or CH$_2$ may be replaced by hydroxy;
X, independently for each occurrence, represents S, O or CH=CH, wherein any hydrogen atom of a CH unit may be replaced by alkyl;
Y, independently for each occurrence, represents H or CH$_2$O(CO)R$_7$;
R$_7$, independently for each occurrence, represents H or substituted or unsubstituted alkyl, alkoxy, aminoalkyl, alkylaminoalkyl, heterocyclylalkyl, or heterocyclylalkoxy;
Z represents H or R$_3$(CO);
R$_1$ and R$_2$ each independently represent H, alkyl, alkoxy or hydroxy;
R$_3$, independently for each occurrence, represents substituted or unsubstituted alkyl, hydroxyalkyl, aminoalkyl, acylaminoalkyl, alkenyl, alkoxy, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, heteroaryloxyalkyl or C(R$_8$)(R$_9$)(R$_{10}$), N(R$_4$)(R$_5$) or OR$_6$, wherein any free hydroxyl group may be acylated to form C(O)R$_7$;

R4 and R5 each independently represent H or substituted or unsubstituted alkyl, hydroxyalkyl, acyl, aminoalkyl, acylaminoalkyl, alkenyl, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, or heteroaryloxyalkyl, wherein any free hydroxyl group may be acylated to form C(O)R7;

R6, independently for each occurrence, represents substituted or unsubstituted alkyl, hydroxyalkyl, aminoalkyl, acylaminoalkyl, alkenyl, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, or heteroaryloxyalkyl, wherein any free hydroxyl group may be acylated to form C(O)R7; and R8, R9 and R10 each independently represent H or substituted or unsubstituted alkyl, hydroxy, hydroxyalkyl, amino, acylamino, aminoalkyl, acylaminoalkyl, alkoxycarbonyl, alkoxycarbonylamino, alkenyl, alkoxy, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, or heteroaryloxyalkyl, or R8 and R9 together with the carbon to which they are attached, form a carbocyclic or heterocyclic ring system, wherein any free hydroxyl group may be acylated to form C(O)R7, and wherein at least two of R8, R9, and R10 are not H.

2. The method of claim 1, wherein conjointly administering the glutaminase inhibitor and the immuno-oncology therapeutic agent provides improved efficacy relative to individual administration of the glutaminase inhibitor or immuno-oncology therapeutic agent as a single agent.

3. The method of claim 2, wherein conjointly administering the immuno-oncology therapeutic agent and glutaminase inhibitor provides an additive effect.

4. The method of claim 2, wherein conjointly administering the immuno-oncology therapeutic agent and glutaminase inhibitor provides a synergistic effect.

5. The method of claim 1, wherein the immuno-oncology therapeutic agent is an inhibitor of arginase, CTLA-4, indoleamine 2,3-dioxygenase, and/or PD-1/PD-L1.

6. The method of claim 1, wherein the immuno-oncology therapeutic agent is selected from abagovomab, adecatumumab, afutuzumab, alemtuzumab, anatumomab mafenatox, apolizumab, blinatumomab, BMS-936559, catumaxomab, durvalumab, epacadostat, epratuzumab, indoximod, inotuzumab ozogamicin, intelumumab, ipilimumab, isatuximab, lambrolizumab, MED14736, MPDL3280A, nivolumab, obinutuzumab, ocaratuzumab, ofatumumab, olatatumab, pembrolizumab, pidilizumab, rituximab, ticilimumab, samalizumab, and tremelimumab.

7. The method of claim 1, wherein L represents CH2CH2.

8. The method of claim 1, wherein Y represents H.

9. The method of claim 1, wherein X, independently for each occurrence, represents S or CH=CH, wherein any hydrogen atom of a CH unit may be replaced by alkyl.

10. The method of claim 1, wherein Z represents R3(CO).

11. The method of claim 10, wherein each occurrence of R3 is not identical.

12. The method of claim 1, wherein R1 and R2 each represent H.

13. The method of claim 1, wherein R3, independently for each occurrence, represents substituted or unsubstituted arylalkyl, heteroarylalkyl, cycloalkyl, or heterocycloalkyl.

14. The method of claim 1, wherein the glutaminase inhibitor is a compound of formula Ia,

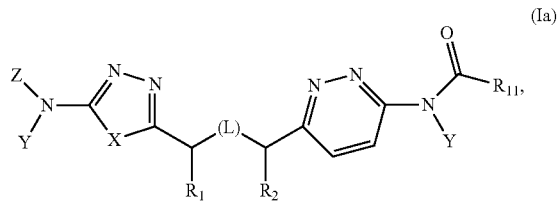

or a pharmaceutically acceptable salt thereof, wherein:

L represents CH2SCH2, CH2CH2, CH2CH2CH2, CH2, CH2S, SCH2, CH2NHCH2, CH=CH, or

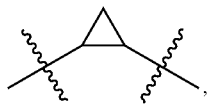 [SMILES: *C1CC1*]

preferably CH2CH2, wherein any hydrogen atom of a CH or CH2 unit may be replaced by alkyl or alkoxy, any hydrogen of an NH unit may be replaced by alkyl, and any hydrogen atom of a CH2 unit of CH2CH2, CH2CH2CH2 or CH2 may be replaced by hydroxy;

X represents S, O or CH=CH, preferably S or CH=CH, wherein any hydrogen atom of a CH unit may be replaced by alkyl;

Y, independently for each occurrence, represents H or CH2O(CO)R7;

R7, independently for each occurrence, represents H or substituted or unsubstituted alkyl, alkoxy, aminoalkyl, alkylaminoalkyl, heterocyclylalkyl, arylalkyl, or heterocyclylalkoxy;

Z represents H or R3(CO);

R1 and R2 each independently represent H, alkyl, alkoxy or hydroxy, preferably H;

R3 represents substituted or unsubstituted alkyl, hydroxyalkyl, aminoalkyl, acylaminoalkyl, alkenyl, alkoxy, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, heteroaryloxyalkyl or C(R8)(R9)(R10), N(R4)(R5) or OR6, wherein any free hydroxyl group may be acylated to form C(O)R7;

R4 and R5 each independently represent H or substituted or unsubstituted alkyl, hydroxyalkyl, acyl, aminoalkyl, acylaminoalkyl, alkenyl, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, or heteroaryloxyalkyl, wherein any free hydroxyl group may be acylated to form C(O)R7;

R6, independently for each occurrence, represents substituted or unsubstituted alkyl, hydroxyalkyl, aminoalkyl, acylaminoalkyl, alkenyl, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, or heteroaryloxyalkyl, wherein any free hydroxyl group may be acylated to form C(O)R7; and R8, R9 and R10 each independently represent H or substituted or unsubstituted alkyl, hydroxy, hydroxyalkyl, amino, acylamino, aminoalkyl, acylaminoalkyl, alkoxycarbonyl, alkoxycarbonylamino, alkenyl, alkoxy, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, or heteroaryloxyalkyl, or $R_8$ and $R_9$ together with the carbon to which they are attached, form a carbocyclic or heterocyclic ring system, wherein any free hydroxyl group may be acylated to form $C(O)R_7$, and wherein at least two of $R_8$, $R_9$ and $R_{10}$ are not H;

$R_{11}$ represents substituted or unsubstituted aryl, arylalkyl, aryloxy, aryloxyalkyl, heteroaryl, heteroarylalkyl, heteroaryloxy, or heteroaryloxyalkyl, or $C(R_{12})(R_{13})(R_{14})$, $N(R_4)(R_{14})$ or $OR_{14}$, wherein any free hydroxyl group may be acylated to form $C(O)R_7$;

$R_{12}$ and $R_{13}$ each independently represent H or substituted or unsubstituted alkyl, hydroxy, hydroxyalkyl, amino, acylamino, aminoalkyl, acylaminoalkyl, alkoxycarbonyl, alkoxycarbonylamino, alkenyl, alkoxy, alkoxyalkyl, aryl, arylalkyl, aryloxy, aryloxyalkyl, cycloalkyl, cycloalkylalkyl, heterocyclyl, heterocyclylalkyl, heteroaryl, heteroarylalkyl, heteroaryloxy, or heteroaryloxyalkyl, wherein any free hydroxyl group may be acylated to form $C(O)R_7$, and wherein both of $R_{12}$ and $R_{13}$ are not H; and $R_{14}$ represents substituted or unsubstituted aryl, arylalkyl, aryloxy, aryloxyalkyl, heteroaryl, heteroarylalkyl, heteroaryloxy, or heteroaryloxyalkyl.

15. The method of claim 1, wherein the glutaminase inhibitor is a compound having the structure of formula (II):

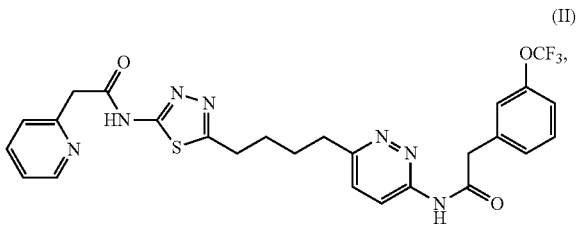 [SMILES: O=C(Cc1cccc(OC(F)(F)F)c1)Nc1ccc(CCCCc2nnc(NC(=O)Cc3ccccn3)s2)nn1]

or a pharmaceutically acceptable salt thereof.

16. The method of claim 1, wherein the cancer is melanoma.

17. The method of claim 1, wherein the cancer is colon cancer.

18. The method of claim 1, further comprising conjointly administering one or more additional chemotherapeutic agents.

19. The method of claim 1, wherein the immuno-oncology therapeutic agent is an anti-PD-L1 antibody and the glutaminase inhibitor is a compound of formula II:

or a pharmaceutically acceptable salt thereof.

20. The method of claim 1, wherein the immuno-oncology therapeutic agent is an anti-PD-1 antibody and the glutaminase inhibitor is a compound of formula II:

or a pharmaceutically acceptable salt thereof.

* * * * *